(12) United States Patent
Yadin

(10) Patent No.: US 7,842,081 B2
(45) Date of Patent: Nov. 30, 2010

(54) STENT WITH SPIRAL SIDE-BRANCH

(75) Inventor: Amnon Yadin, Kfar Vitkin (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 195 days.

(21) Appl. No.: 11/604,613

(22) Filed: Nov. 27, 2006

(65) Prior Publication Data

US 2007/0112419 A1 May 17, 2007

Related U.S. Application Data

(63) Continuation-in-part of application No. 11/273,186, filed on Nov. 14, 2005.

(51) Int. Cl.
*A61F 2/06* (2006.01)
(52) U.S. Cl. .................... 623/1.35; 623/1.15
(58) Field of Classification Search ............... 623/1.15, 623/1.16, 1.35
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,441,515 A | 8/1995 | Khosravi et al. | |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,596,020 A | 1/1997 | Morris et al. | 541/646 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |

(Continued)

FOREIGN PATENT DOCUMENTS

CA 2220864 7/1999

(Continued)

OTHER PUBLICATIONS

U.S. Appl. No. 60/844,011, filed Sep. 12, 2006, Broome et al.

(Continued)

*Primary Examiner*—Gary Jackson
*Assistant Examiner*—David Eastwood
(74) *Attorney, Agent, or Firm*—Vidas, Arrett & Steinkraus, P.A.

(57) ABSTRACT

In at least one embodiment, a stent comprises a plurality of interconnected framework members defining a plurality of cells. A portion of the interconnected framework members comprise a side branch structure having an inner side branch cell that is shaped differently from other cells of the stent. The side branch structure further comprises a serpentine ring extending around the inner side branch cell, the serpentine ring having alternating struts and turns. Each strut includes curvature along its length and is oriented with the curvature being concave with respect to a center point of the inner side branch cell.

8 Claims, 28 Drawing Sheets

U.S. PATENT DOCUMENTS

| | | | |
|---|---|---|---|
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,922,021 A | 7/1999 | Jang | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,013,091 A | 1/2000 | Ley et al. | 606/191 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,433 A | 3/2000 | Ehr et al. | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,059,825 A | 5/2000 | Hobbs et al. | |
| 6,063,111 A | 5/2000 | Hieshima et al. | |
| 6,068,655 A | 5/2000 | Seguin et al. | 623/1 |
| 6,086,611 A | 7/2000 | Duffy et al. | 623/1 |
| 6,090,127 A | 7/2000 | Globerman | 606/194 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,231,599 B1 | 5/2001 | Ley | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,822 B1 | 12/2001 | Chouinard et al. | 623/1.35 |
| 6,325,826 B1 | 12/2001 | Vardi et al. | 623/1.35 |
| 6,334,864 B1 | 1/2002 | Amplatz et al. | 606/200 |
| 6,334,870 B1 | 1/2002 | Ehr et al. | 623/1.16 |
| 6,346,089 B1 | 2/2002 | Dibie | 603/1.15 |
| 6,348,065 B1 | 2/2002 | Brown et al. | 623/1.16 |
| 6,348,086 B1 | 2/2002 | Harms et al. | 96/125 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,478,816 B1 | 11/2002 | Kveen et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Cho et al. | 623/1.15 |
| 6,776,793 B2 | 8/2004 | Brown et al. | 623/1.15 |
| 6,805,704 B1 | 10/2004 | Hoyns | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |

| Publication No. | Date | Inventor | Class |
|---|---|---|---|
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker et al. | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0138737 A1* | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1 | 12/2004 | Davidson et al. | 623/1.15 |
| 2005/0004656 A1 | 1/2005 | Das | 623/1.16 |
| 2005/0010278 A1 | 1/2005 | Vardi et al. | 623/1.35 |
| 2005/0015108 A1 | 1/2005 | Williams et al. | 606/194 |
| 2005/0015135 A1 | 1/2005 | Shanley | 623/1.11 |
| 2005/0060027 A1 | 3/2005 | Khenansho et al. | 623/1.35 |
| 2005/0096726 A1 | 5/2005 | Sequin et al. | 623/1.12 |
| 2005/0102021 A1 | 5/2005 | Osborne | 623/1.13 |
| 2005/0102023 A1 | 5/2005 | Yadin et al. | 623/1.11 |
| 2005/0119731 A1 | 6/2005 | Brucker et al. | 623/1.35 |
| 2005/0125076 A1 | 6/2005 | Ginn | 623/23.65 |
| 2005/0131423 A1 | 6/2005 | Yachia et al. | |
| 2005/0131526 A1 | 6/2005 | Wong | 623/1.15 |
| 2005/0149161 A1 | 7/2005 | Eidenschink et al. | 623/1.11 |
| 2005/0154442 A1 | 7/2005 | Eidenschink et al. | 623/1.11 |
| 2005/0154444 A1 | 7/2005 | Quadri | 623/1.13 |
| 2005/0183259 A1 | 8/2005 | Eidenschink et al. | 29/508 |
| 2005/0209673 A1 | 9/2005 | Shaked | 623/1.11 |
| 2005/0228483 A1* | 10/2005 | Kaplan et al. | 623/1.15 |
| 2006/0036315 A1 | 2/2006 | Yadin et al. | 623/1.35 |
| 2006/0041303 A1 | 2/2006 | Israel | 623/1.11 |
| 2006/0079956 A1 | 4/2006 | Eigler et al. | 623/1.35 |
| 2006/0173528 A1 | 8/2006 | Feld et al. | 623/1.15 |
| 2007/0005125 A1 | 1/2007 | Berenstein et al. | |
| 2007/0073376 A1 | 3/2007 | Krolik et al. | 623/1.11 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |

| | | |
|---|---|---|
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

U.S. Appl. No. 11/519,552, filed Sep. 12, 2006, Brown et al.
Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).
Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).
Caputo, Ronald P., "Stent Jail: A Minimum-Security Prison," *The American Journal of Cardiology*, vol. 77, pp. 1226-1230 (Jun. 1, 1996).
Colombo, M.D., Antonio, "Kissing Stent for Bifurcational Coronary Lesion," *Catheterization and Cardiovascular Diagnosis*, vol. 30, pp. 327-330 (Dec. 1993).
Carrie, M.D., Didier, "T-Shaped Stent Placement: A Technique for the Treatment of Dissected Bifurcation Lesions," *Catheterization and Cardiovascular Diagnosis*, vol. 37, pp. 311-313 (Mar. 1996).
Katoh, M.D., Osamu, "New Double Wire Technique to Stent Ostial Lesions," *Catheterization and Cardiovascular Diagnosis*, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).
Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).
Satler, M.D., Lowell F., "Bifurcation Disease: To Treat or Not to Treat," *Catheterization and Cardiovascular Interventions*, vol. 50, pp. 411-412 (2000).
U.S. Appl. No. 09/663,111, filed Sep. 15, 2000, Davidson et al.
U.S. Appl. No. 09/614,472, filed Jul. 11, 2000, Davidson et al.
U.S. Appl. No. 09/325,996, filed Jun. 4, 1999, Vardi et al.

* cited by examiner

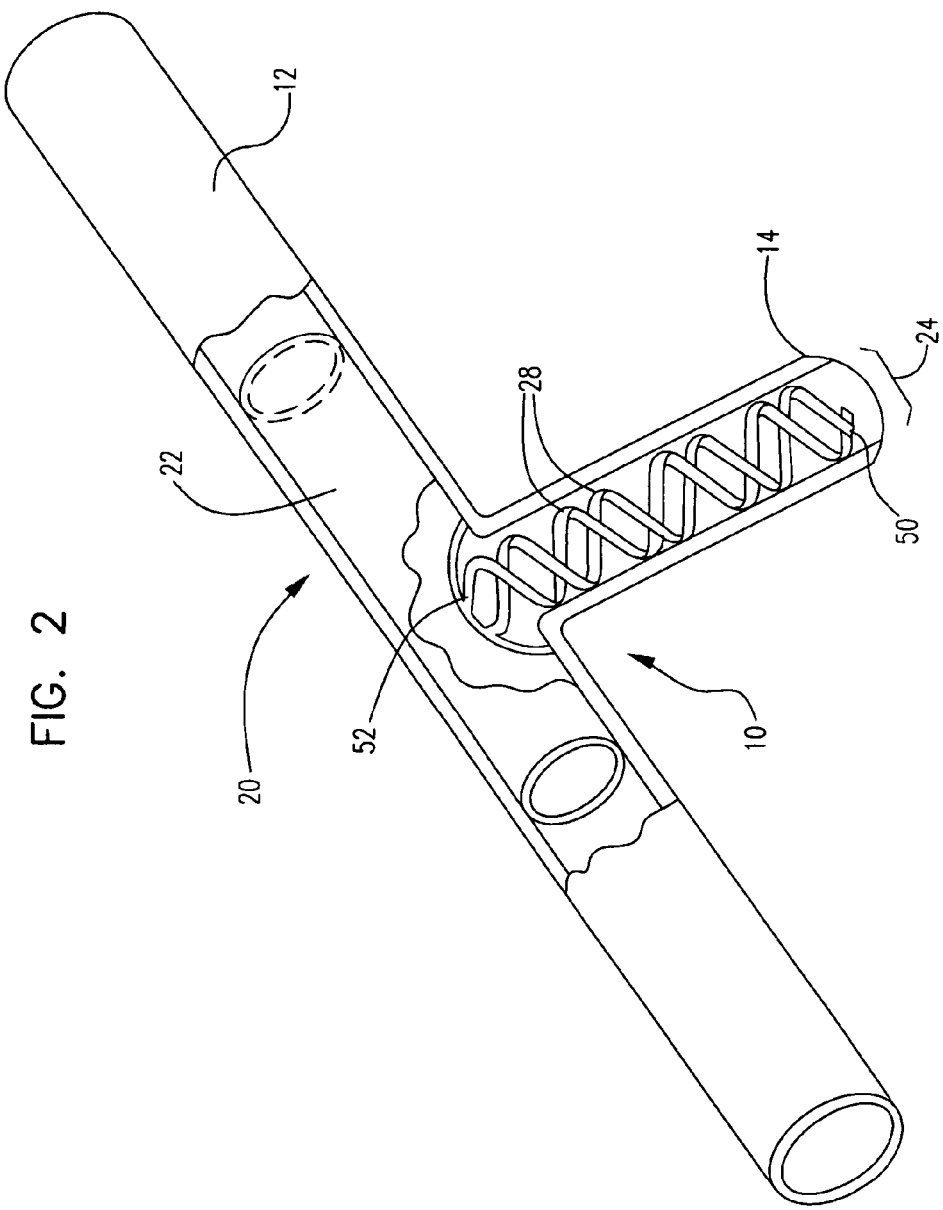

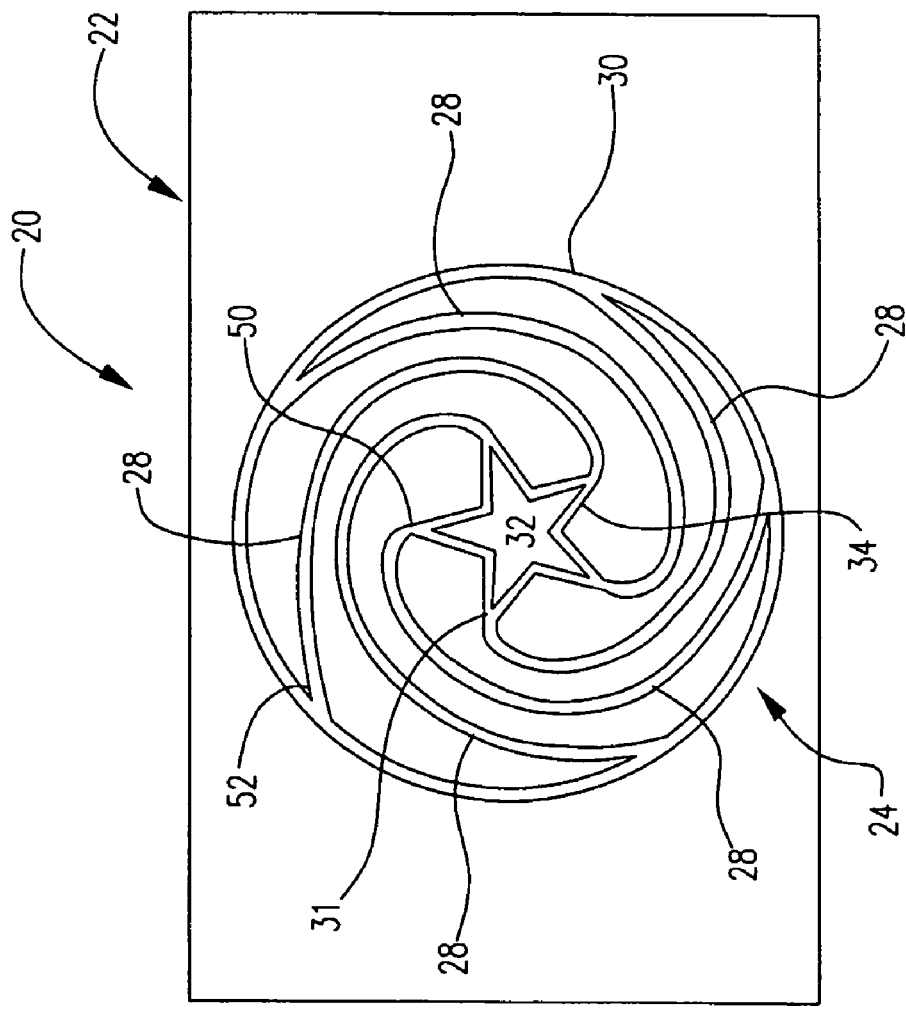

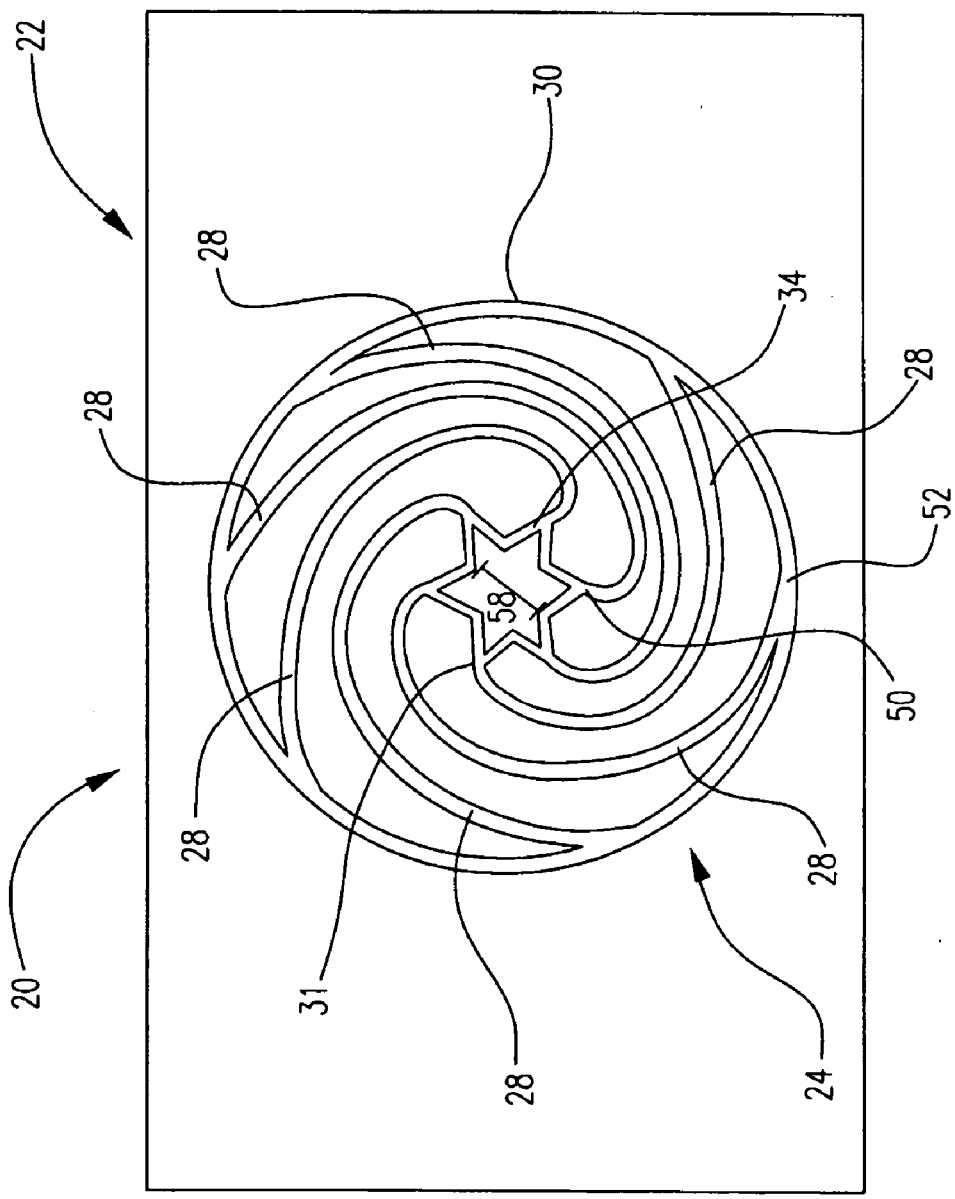

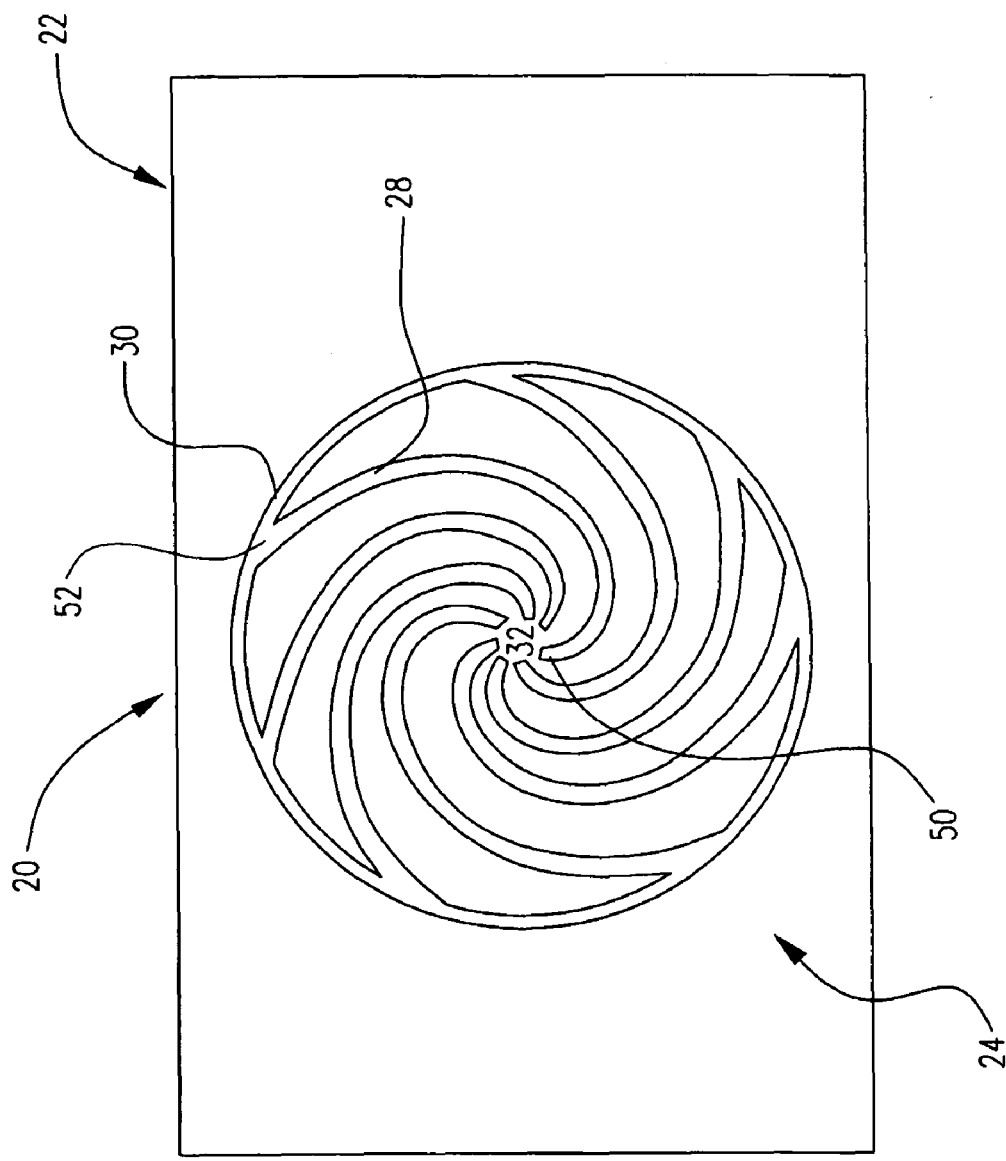

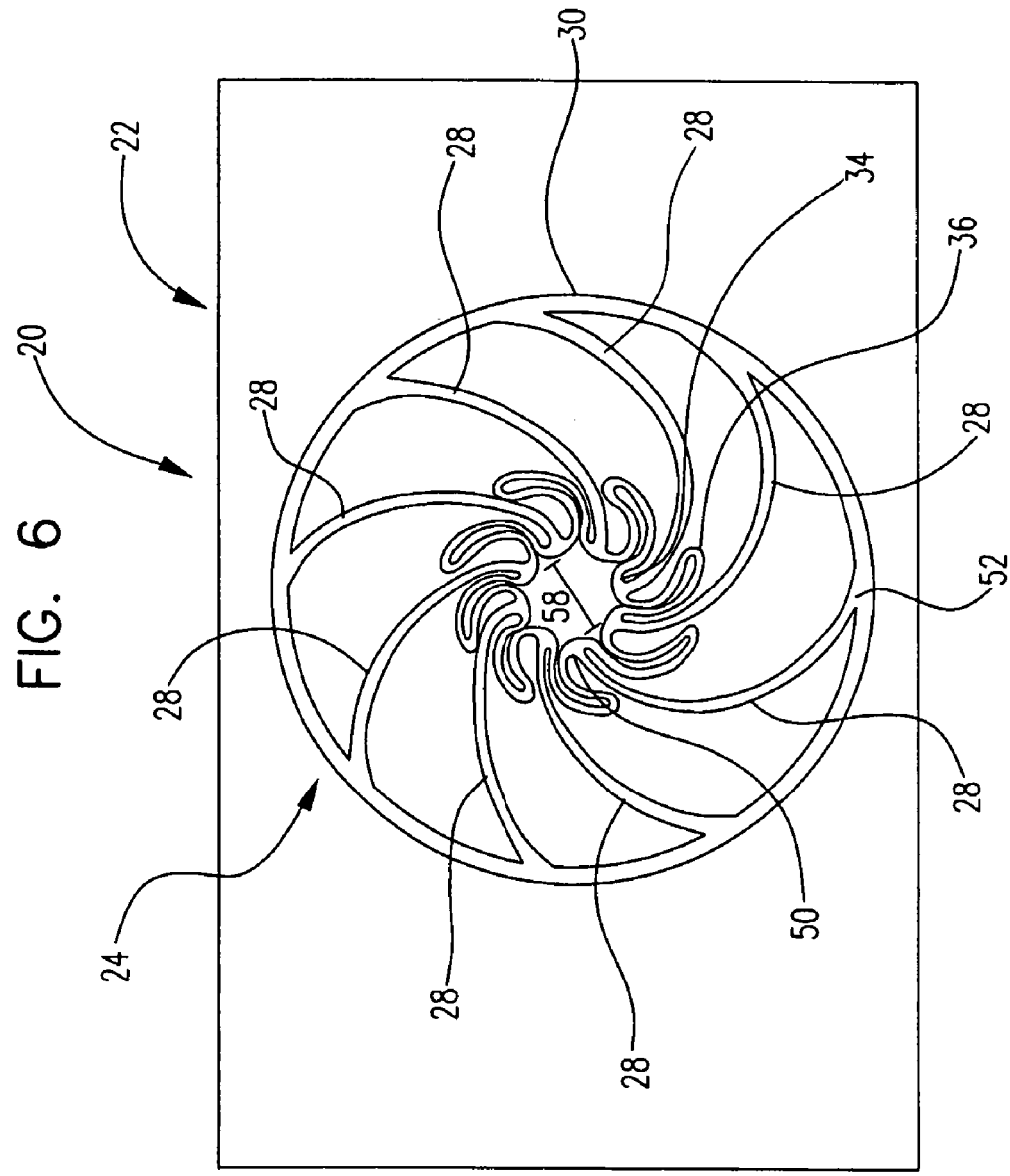

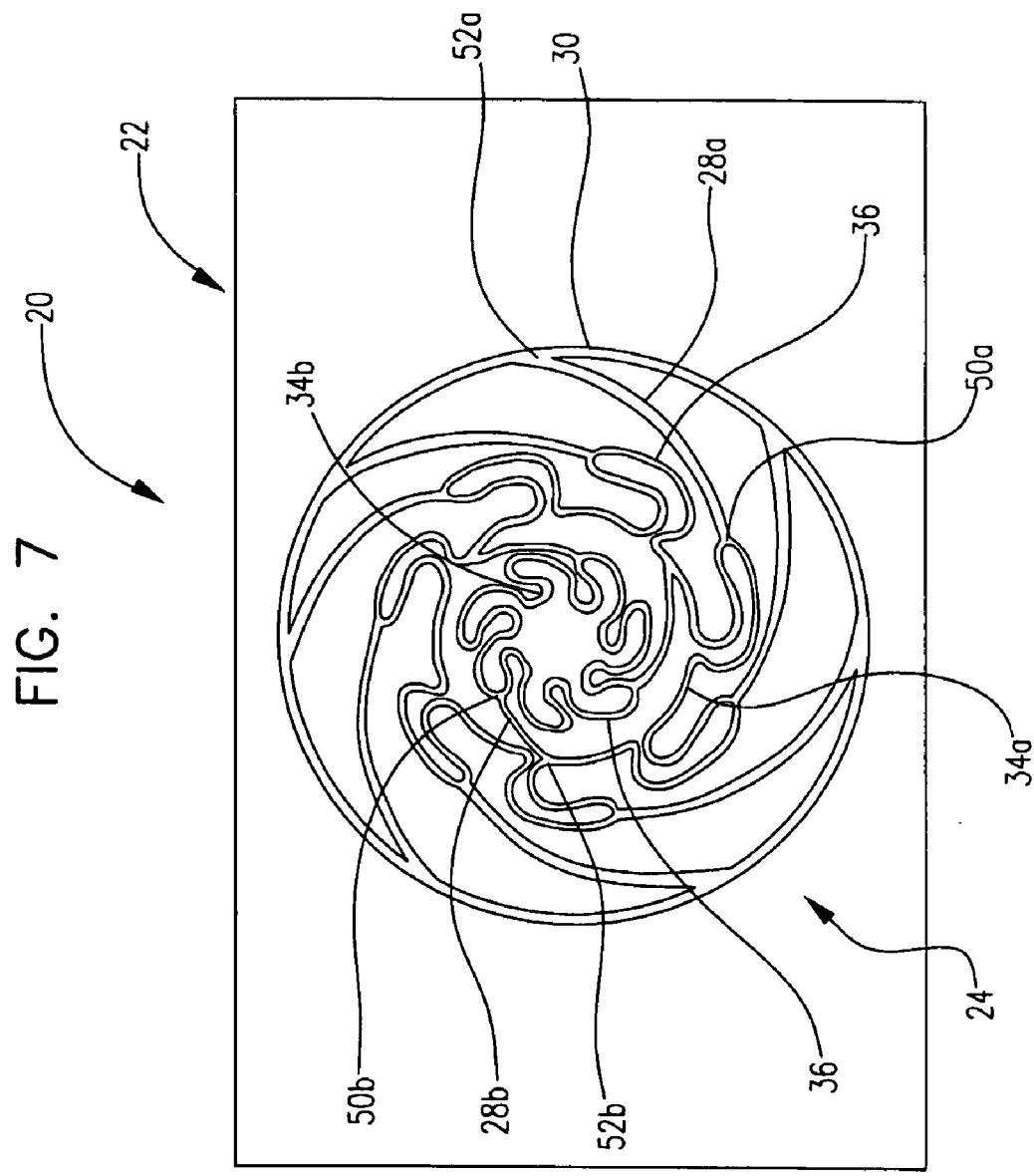

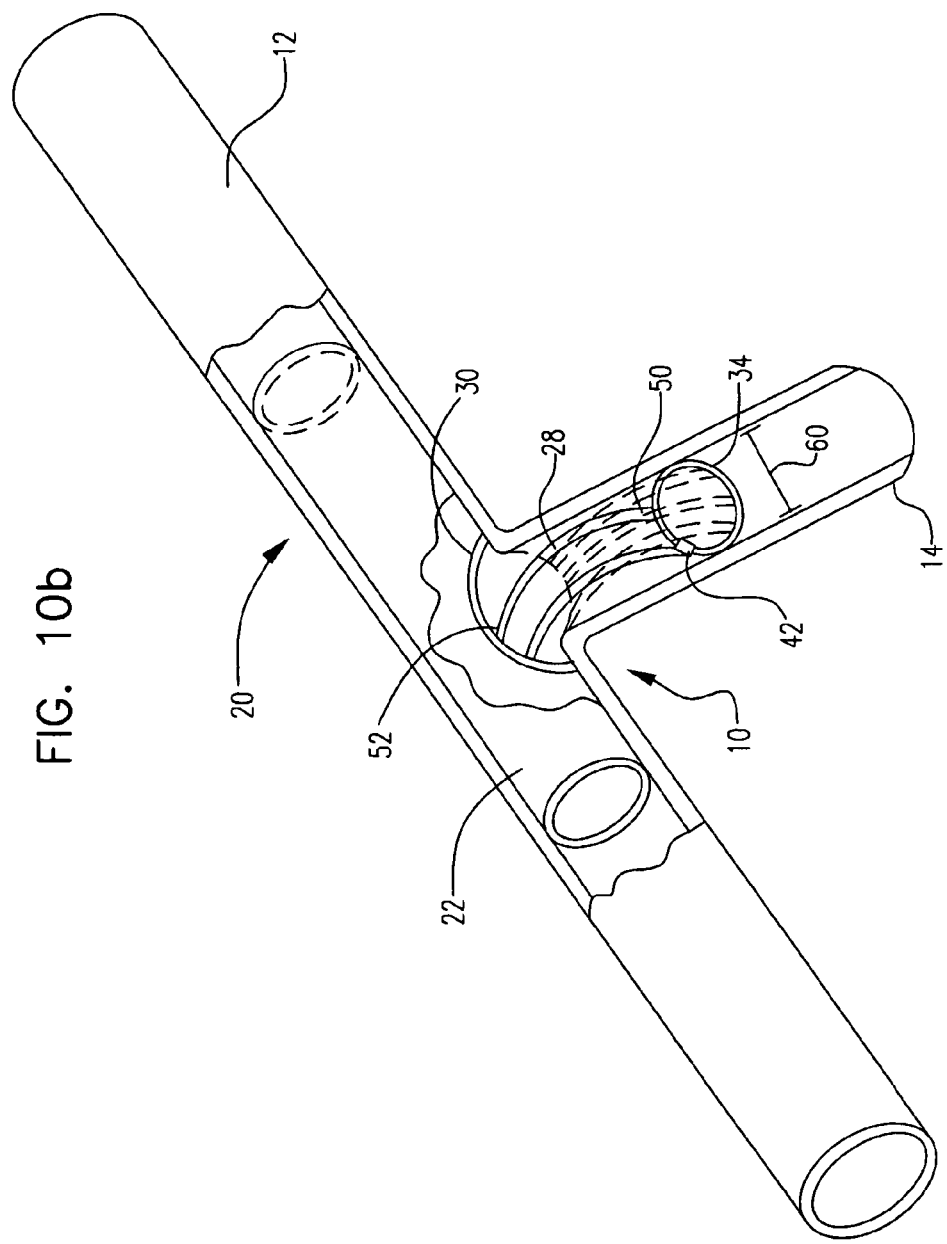

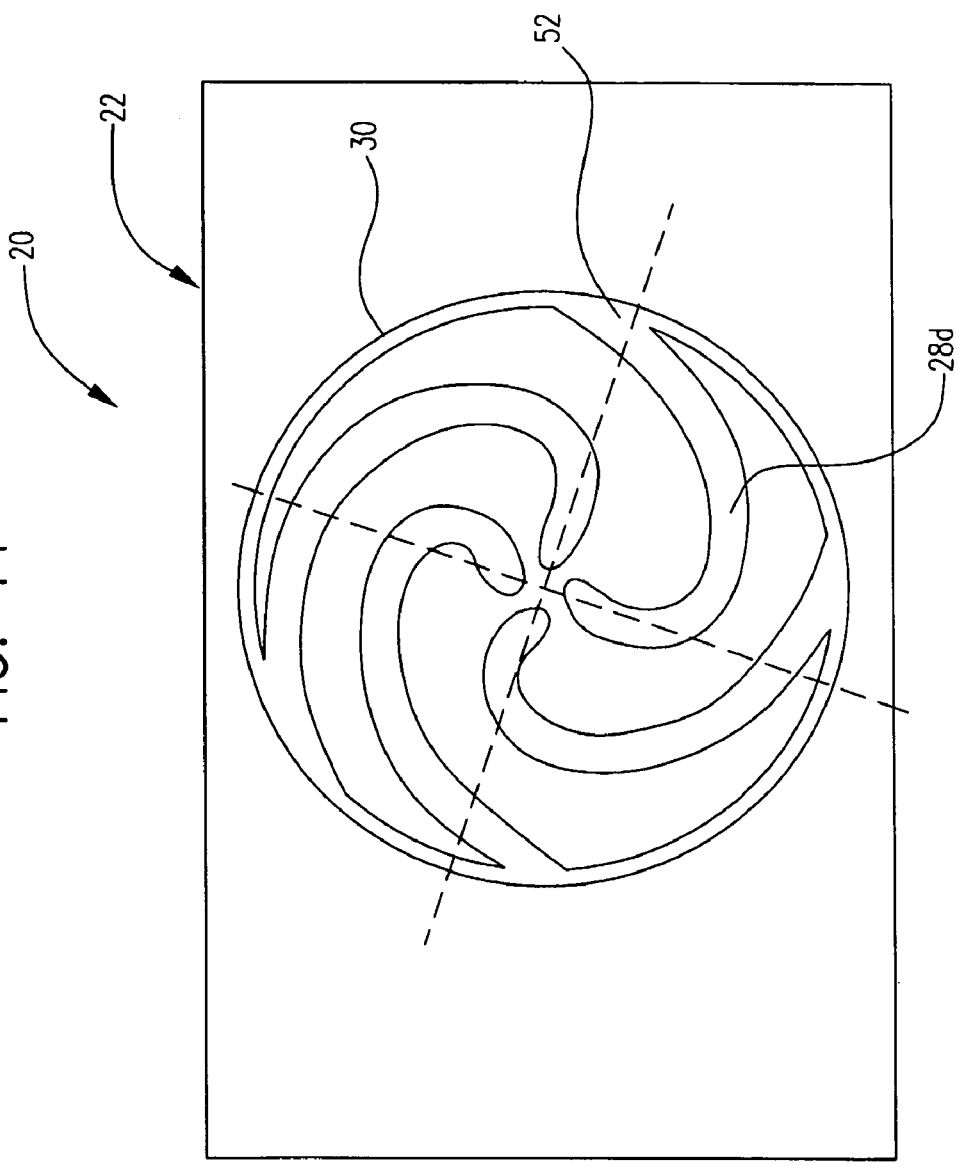

STENT WITH SPIRAL SIDE-BRANCH

CROSS-REFERENCE TO RELATED APPLICATIONS

This Application claims the benefit of and is a continuation-in-part of U.S. patent application Ser. No. 11/273186, filed Nov. 14, 2005, the entire contents of which is hereby incorporated herein by reference.

STATEMENT REGARDING FEDERALLY SPONSORED RESEARCH

Not Applicable

BACKGROUND OF THE INVENTION

Stents, grafts, stent-grafts and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding or expanded by an internal radial force, such as when mounted on a balloon.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nitinol, shape memory polymers, etc. Stents may also be formed in a variety of manners as well. For example, a stent may be formed by etching or cutting the stent pattern from a tube or section of stent material; a sheet of stent material may be cut or etched according to a desired stent pattern whereupon the sheet may be rolled or other wise formed into the desired tubular or bifurcated tubular shape of the stent; one or more wires or ribbons of stent material may be braided or otherwise formed into a desired shape and pattern.

Within the vasculature however, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcations, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs that are suitable for placement at a vessel bifurcation.

All U.S. patents and applications and all other published documents mentioned anywhere in this application are incorporated herein by reference in their entirety Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of interconnected framework members defining a plurality of cells. A portion of the interconnected framework members comprise a side branch structure having an inner side branch cell that is shaped differently from other cells of the stent. The side branch structure further comprises a serpentine ring extending around the inner side branch cell, the serpentine ring having alternating struts and turns. Each strut includes curvature along its length and is oriented with the curvature being concave with respect to a center point of the inner side branch cell.

In at least one other embodiment, a stent comprises a plurality of interconnected expandable framework members and a side branch structure. The side branch structure defines an inner side branch cell that is shaped differently from other cells of the stent. The side branch structure comprises a serpentine ring and a plurality of side branch connectors. The serpentine ring comprises alternating struts and turns, each strut being concave with respect to a center point of the inner side branch cell. Each side branch connector connects between a turn of the serpentine ring and at least one expandable framework member.

In at least one other embodiment, a stent comprises a first end region, a second end region and a central region. Each region comprises a plurality of serpentine bands, and the central region further comprises a side branch structure. The side branch structure includes a first parabolic support strut, a second parabolic support strut, a serpentine ring and a plurality of side branch connectors. The serpentine ring extends around a side branch center point. Each parabolic support strut is concave with respect to the side branch center point. Each serpentine band in the central region is connected at one end to a parabolic support strut and at the other end to the same parabolic support strut. Each side branch connector connects between the serpentine ring and a parabolic support strut.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 2 is a view of the stent with a spiral side branch section that has a plurality of spiral arms in the expanded state.

FIG. 3 is a side view of the stent with a spiral side branch section that has a circumferential member engaged to a plurality of spiral arms in the unexpanded state.

FIG. 4 is a side view of the stent with another embodiment of the spiral side branch section of FIG. 3 in the unexpanded state.

FIG. 5 is a side view of the stent with a spiral side branch section that has a plurality of spiral arms with free ends in the unexpanded state.

FIG. 6 is a side view of the stent with a spiral side branch section that has a plurality of spiral arms and a circumferential member with a serpentine shape in the unexpanded state.

FIG. 7 is a side view of the stent with a spiral side branch section that has a plurality of serpentine shaped circumferential members and a plurality of spiral arms in an unexpanded state.

FIG. 8b shows a locking mechanism which may be used in the stent of FIG. 8a.

FIG. 10b is a side view of the stent of FIG. 8a with the spiral branch section in an expanded state, the spiral arms are curved when in an expanded state.

FIG. 11 is a side view of the stent with a spiral side branch section in an unexpanded state consisting of four spiral arms.

DETAILED DESCRIPTION OF THE INVENTION

Figure 1:
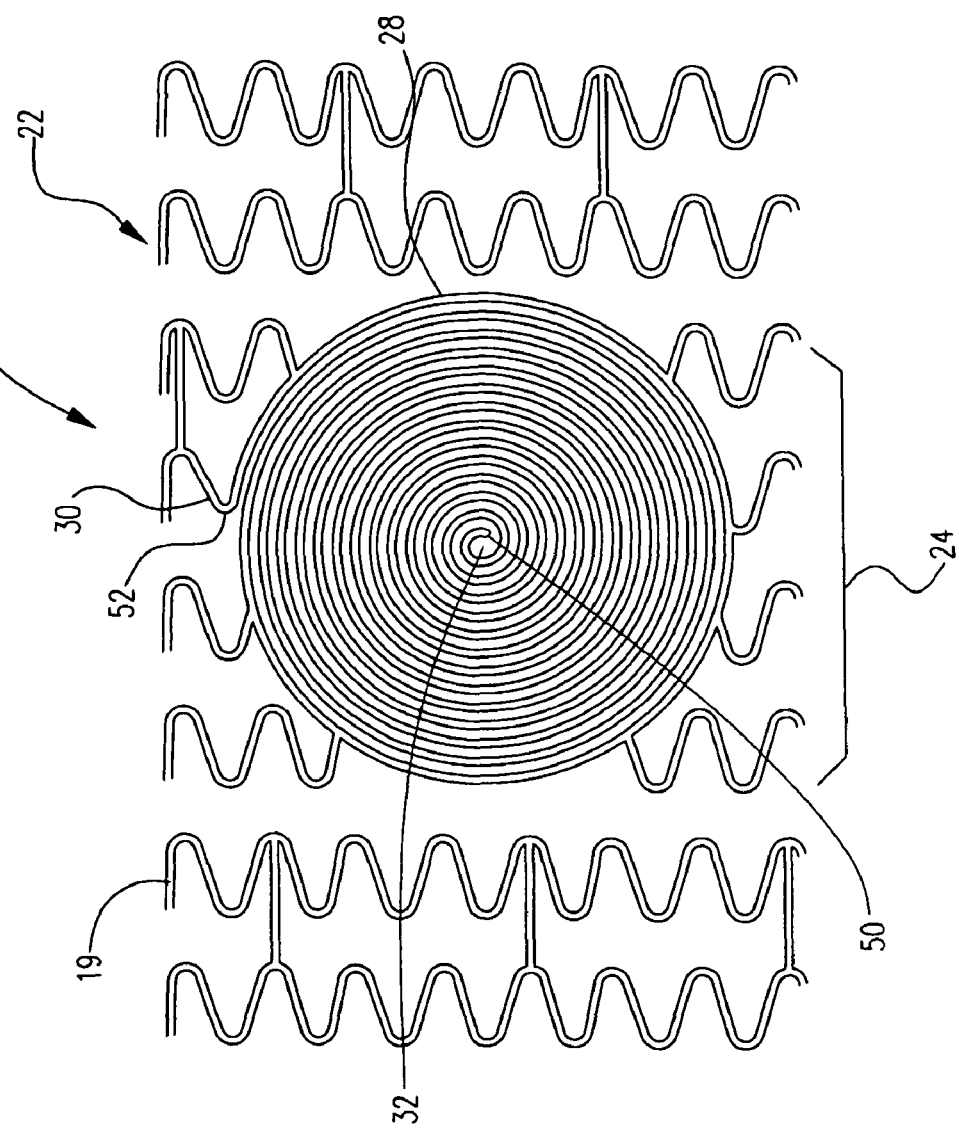
FIG. 1 is a side view of the stent with a spiral side branch section that has one spiral arm in the unexpanded state.

While this invention may be embodied in many different forms, there are described in detail herein specific embodiments of the invention. This description is an exemplification of the principles of the invention and is not intended to limit the invention to the particular embodiments illustrated.

For purposes of this disclosure, like reference numerals in the figures shall refer to like features unless otherwise indicated.

Some examples of stents having a side opening and methods of deploying such stents are disclosed in U.S. Pat. Nos. 5,596,020 and 6,835,203, the entire disclosures of which are hereby incorporated herein in their entireties.

The entire disclosures of U.S. Pat. Nos. 5,922,021, 6,123,721, 6,334,870, 6,478,816, 6,348,065 and 6,325,826 are hereby incorporated herein by reference in their entireties. The entire disclosures of U.S. Provisional Application No. 60/844,011, filed Sep. 12, 2006, and U.S. patent application Ser. No. 11/519,552, filed Sep. 12, 2006, are hereby incorporated herein by reference in their entireties.

As used herein the term 'stent' refers to an expandable prosthesis for implantation into a body lumen or vessel and includes devices such as stents, grafts, stent-grafts, vena cava filters, expandable frameworks, etc.

Referring now to the drawings which are for the purposes of illustrating embodiments of the invention only and not for purposes of limiting same, in at least one embodiment of the invention, an example of which is shown in FIG. 1, stent 20, shown in side view, comprises an expandable spiral side branch support section 24. Expandable spiral side branch support section 24 has a spiral configuration and is disposed about a center opening 32 and center point. The center point is located at a first longitudinal coordinate and a first circumferential coordinate. The longitudinal coordinate indicates where, along the length of the stent, the center point is located. The circumferential coordinate indicates where, about the circumference of the stent, the center point lies. The spiral side branch support section 24 comprises at least one spiral arm 28 forming a curve extending at least partially around the center point. The at least one spiral arm has a first end and a second end. One of the two ends is positioned closer to the center point than the other of the two ends.

The stent of FIG. 1 has no more than one spiral branch support section 24 located at the first longitudinal coordinate. Thus, there are no other spiral branch support sections which are disposed about the circumference of the stent and located at the first longitudinal coordinate. In other embodiments of the invention, additional spiral branch support sections may be located at the first longitudinal coordinate or any other longitudinal and circumferential coordinate. Moreover, the spiral side branch support section 24 has only one spiral arm 28.

The outer support member 30 can have any shape, for example a shape that corresponds to the cellular design of the primary stent section 22, a circular shape, or a serpentine shape. The outer support member 30 of FIGS. 2-13 has a circular shape. The outer support member 30 of FIGS. 2-13 has at least one spiral arm 28 extending therefrom. If the spiral side branch section 24 has circumferential members 34, the circumferential members 34 can have any shape. In at least one embodiment, all the circumferential members 34 have the same shape.

Figure 14:
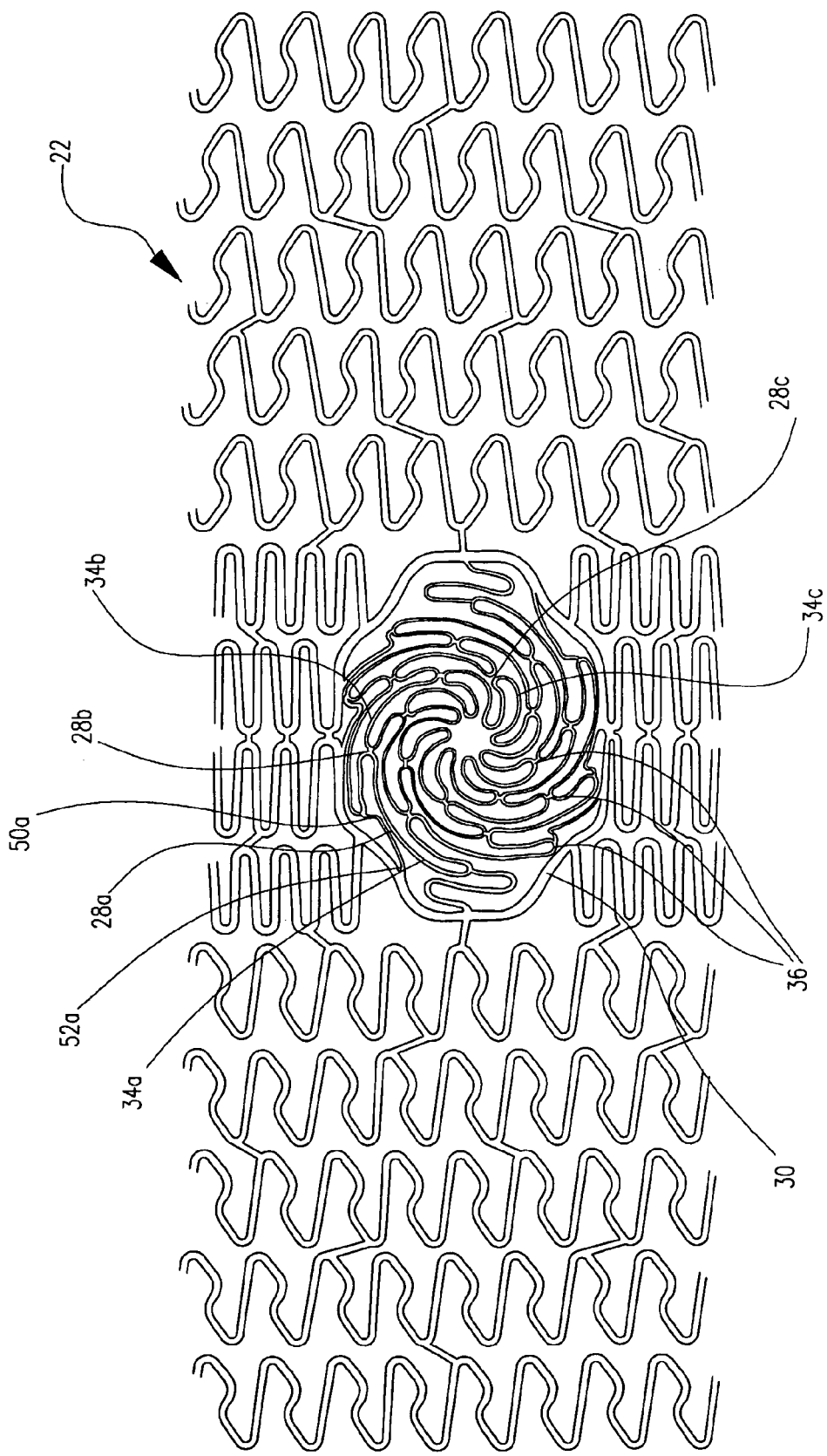
FIG. 14 is a side view of an embodiment of the stent with a spiral side branch section that has a plurality of serpentine shaped circumferential members and a plurality of spiral arms in an unexpanded state.

Any suitable stent geometry may be used for the main body of the stent. The pattern of interconnected serpentine bands 19 shown is shown by way of example only. The struts that form the serpentine band may be straight as shown in FIG. 1 or may be bent. The stent of FIG. 14 shows straight and bent struts.

If the spiral arm 28 has sufficient length, the spiral arm 28 will form a spiral around the opening 32 in the spiral side branch section 24. Each spiral arm 28 has a distal end 50 and a proximal end 52. The distal end 50 of the spiral arm 28 is positioned closer to the center of the opening 32 of the spiral side branch section 24 than the proximal end 52.

A non-bifurcated stent is formed when only the primary branch section 22 is in an expanded state. A bifurcated stent is formed when both the primary branch section 22 and the spiral side branch section 24 are in an expanded state.

In FIG. 1, the primary branch section 22 and the spiral side branch section 24 are shown in an unexpanded state. The spiral side branch section 24 has an outer support member 30 and one spiral arm 28. The proximal end 52 of the spiral arm 28 is engaged to the outer support member 30. The distal end 50 of the spiral arm 28 is closer to the center of the opening 32 of the spiral side branch section 24 than the proximal end 52.

More generally, the stent of FIG. 1 may have more than one spiral side branch section. Where there is a plurality of side branch sections, the side branches may be disposed at different locations along the length of the stent, different circumferential locations about the stent or both. Where a plurality of side branch sections is present, the side branches may be of the same length or of different lengths. The side branch sections may have only one spiral arm per side branch section or one or more of the side branch sections may each have a plurality of spiral arms.

The stent of FIG. 1 may prove to be advantageous as compared with some of the known petal designs for bifurcated stents. In the case of the latter stents, some of the petals typically have to be bent at an angle in excess of 90 degrees resulting in high stresses on those petals. No such extreme bending occurs during deployment of the stent of FIG. 1 as well as during deployment of other stents disclosed herein.

Another embodiment of the invention is shown at 20 in FIG. 2. Stent 20, shown in an expanded state, has a primary branch section 22 and a spiral side branch section 24 that extends from the primary branch section 22. The primary branch section 22 is a substantially tubular body disposed about a longitudinal axis. Those skilled in the art will recognize that the pattern of the primary branch section 22 can have any cellular design. In some embodiments of the invention, the primary branch section 22 may be characterized as a substantially solid or porous tubular member.

The expandable primary branch section 22 has a first diameter in an unexpanded state (not shown) and a second diameter in an expanded state. In an unexpanded state of the stent, the entirety of the spiral side branch section 24 forms a part of the surface of the substantially tubular body of the primary branch section 22. The unexpanded version of the stent has only one longitudinal flowpath and does not include a portion which branches off of the longitudinal flowpath.

The spiral side branch section 24 has an outer support member 30 and at least one spiral arm 28 that curves around an opening 32 in the spiral side branch section 24.

In FIG. 2 the primary branch section 22 and the spiral side branch section 24 are shown in an expanded state. The spiral side branch section 24 of the stent 20 has an outer support member 30 and a plurality of spiral arms 28. The proximal end 52 of each spiral arm 28 is engaged to the outer support member 30. When the spiral side branch section 24 is in an expanded state the spiral arms 28 form a plurality of helices depending upon the number of spiral arms 28.

Another embodiment of the invention is shown in an unexpanded state in side view in FIG. 3. In the embodiment of FIG. 3, the primary branch section 22 and the spiral side branch section 24 are shown in an unexpanded state. The spiral side branch section 24 has an outer support member 30, a plurality of spiral arms 28 and a circumferential member 34. The shape of the circumferential member 34 is a 5 point star. The proximal ends 52 of the spiral arms 28 are engaged to the outer support member 30. The distal ends 50 of the spiral arms 28 may be engaged to the circumferential member 34 either at the apexes of the star shaped circumferential member 34 or between the apexes of the star shaped circumferential member 34.

Further as shown in FIG. 3, the spiral arms 28 are engaged to the circumferential member 34 at the apexes 31. In addition, the circumferential member 34 bounds a first area 58 in an unexpanded state. The first area 58 is smaller than the area bounded by the circumferential member 34 in an expanded state.

Another embodiment of the invention is shown in side view in FIG. 4. In the embodiment of FIG. 4, the primary branch section 22 and the spiral side branch section 24 are shown in an unexpanded state. Spiral side branch section 24 includes a circumferential member 34 that is a 6 point star.

In some embodiments, the invention is also directed to a stent having a side wall with a plurality of openings therethrough, at least one of the openings being in the form of a star-shaped opening bounded by a star shaped member. The star-shaped opening may be a star with three to nine points, as shown by way of example in FIG. 3 by a five pointed star, or a six pointed star shown in FIG. 4. Typically, there will be additional expandable structure connecting the star shaped structure to the remainder of the stent. The additional structure is configured to be expandable to form a side branch.

The stent typically will have the star shaped opening in the unexpanded state. Desirably, the stent may be expanded to form a main body and a side branch extending therefrom. The side branch may be formed by disposing a balloon catheter through the side branch terminating in the star shaped opening and inflating the balloon. Where the stent is self-expanding, the side branch structure may be allowed to self-expand.

In the embodiment of FIG. 5, the primary branch section 22 and the spiral side branch section 24 are shown in an unexpanded state. The spiral side branch section 24 has an outer support member 30 and a plurality of spiral arms 28. The proximal ends 52 of the spiral arms are engaged to the outer support member 30. The distal ends 50 of the spiral arms 28 are free ends.

In one or more embodiments, the invention is directed to a stent comprising a plurality of spiral arms with free ends, as shown by way of example in FIG. 5. The stent may be in an unexpanded or expanded state (not shown). In an expanded state, the free ends extend outward from a main body of the stent and form a side branch.

In the embodiment of FIG. 6, the primary branch section 22 and the spiral side branch section 24 are shown in an unexpanded state. The spiral side branch section 24 has an outer support member 30, a plurality of spiral arms 28 and a circumferential member 34 with a serpentine shape that has turns 36. The proximal ends 52 of the spiral arms 28 are engaged to the outer support member 30. The distal ends 50 of the spiral arms 28 are engaged to the circumferential member 34 between the turns 36. Alternatively the distal ends 50 of the spiral arms 28 may be engaged to the circumferential member 34 at the turns 36. The circumferential member 34 has first diameter 58 in an unexpanded state as measured by the distance between opposite turns. The first diameter 58 is smaller than the diameter of the circumferential member 34 in an expanded state.

In some embodiments, the invention is also directed to a stent having a side branch section 24 with alternating ring members 34 and spiral arms 28 between the alternating ring members 34, as shown by way of example in FIGS. 7 and 14. The embodiment in FIG. 14 shows a side branch with three concentric rings 34*a,b,c* and three sets of spiral arms 28*a,b,c*. It is within the scope of the embodiment to have more than three concentric rings and three sets of spiral arms. In the embodiment of FIG. 7 the primary branch section 22 and the spiral side branch section 24 are shown in an unexpanded state. The spiral side branch section 24 has an outer support member 30, a plurality of spiral arms 28*a*, each spiral arm having a distal end 50*a* and a proximal end 52*a*, a circumferential member 34*a* with a serpentine shape that has turns 36, a plurality of spiral arms 28*b*, each spiral arm 28*b* having a distal end 50*b* and a proximal end 52*b*, and a circumferential member 34*b* with a serpentine shape that has turns 36.

The proximal ends 52*a* of the spiral arms 28*a* are engaged to the outer support member 30. The distal ends 50*a* of the spiral arms 28*a* are engaged to the turns 36 of the circumferential member 34*a*. The proximal ends 52*b* of the spiral arms 28*b* are engaged to the circumferential member 34*a* between the turns 36. The distal ends 50*b* of the spiral arms 28*b* are engaged to the circumferential member 34*b* at the turns 36.

In the embodiment of FIG. 14, the primary branch section 22 and the spiral side branch section 24 are shown in an unexpanded state. The spiral side branch section 24 has an outer support member 30, a plurality of spiral arms 28*a*, each spiral arm having a distal end 50*a* and a proximal end 52*a*, a circumferential member 34*a* with a serpentine shape that has turns 36, a plurality of spiral arms 28*b*, each spiral arm 28*b* having a distal end and a proximal end, a circumferential member 34*b* with a serpentine shape that has turns 36, a plurality of spiral arms 28*c*, each spiral arm 28*c* having a distal end and a proximal end.

Figure 15:
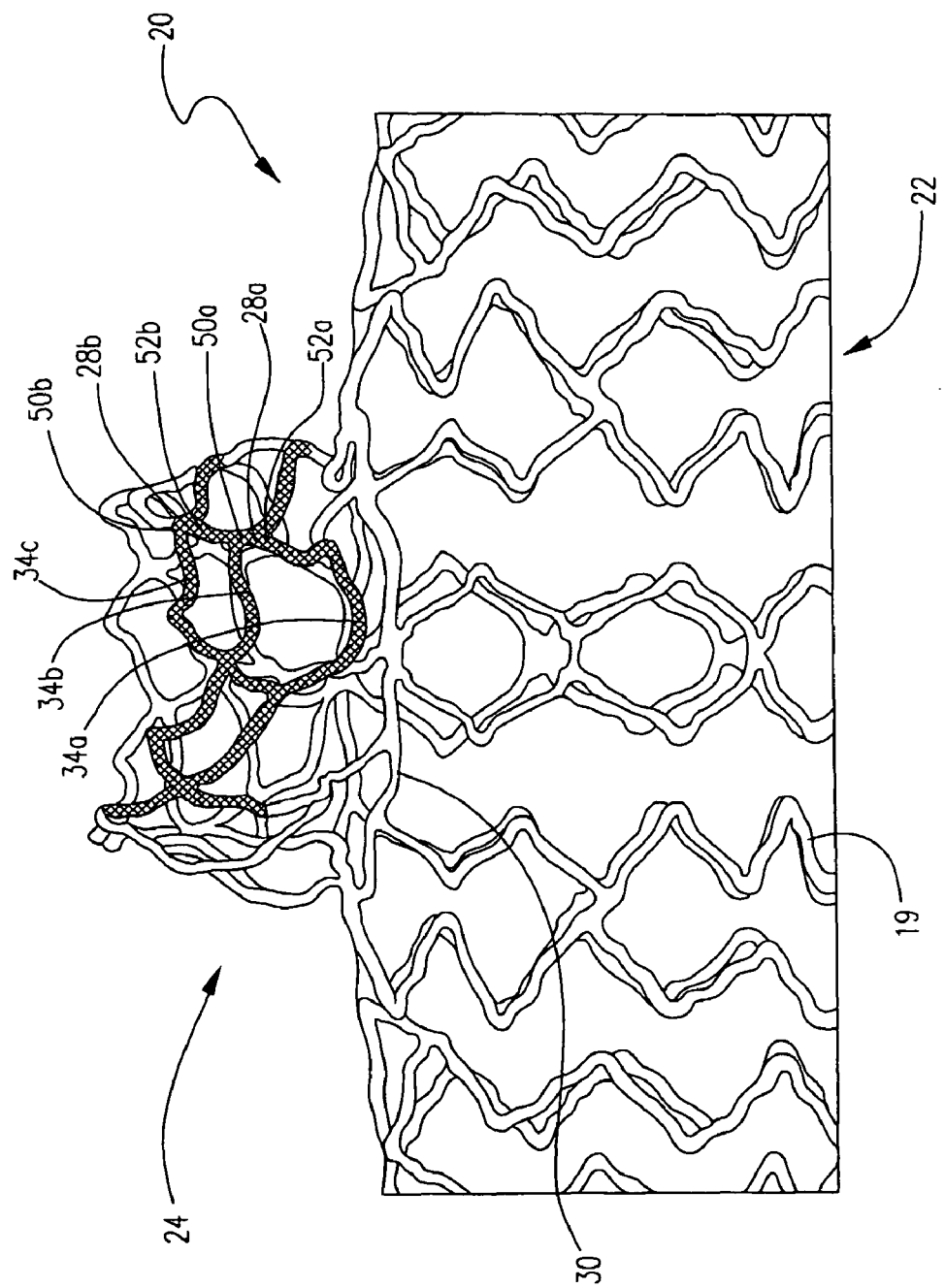
FIG. 15 is a perspective view of the embodiment in FIG. 14 in an expanded state.

The proximal ends 52*a* of the spiral arms 28*a* are engaged to the outer support member 30. The distal ends 50*a* of the spiral arms 28*a* are engaged to the turns 36 of the circumferential member 34*a*. The proximal ends of the spiral arms 28*b* are engaged to the turns 36 of the circumferential member 34*a*. The distal ends of the spiral arms 28*b* are engaged to the turns 36 of the circumferential member 34*b*. The proximal ends of the spiral arms 28*c* are engaged to the turns 36 of the circumferential member 34*b*. The distal ends of the spiral arms 28*c* are engaged to the turns of the circumferential member 34*c*. FIG. 15 shows the embodiment of the spiral branch section in FIG. 14 in an expanded state.

In at least one embodiment, there is an intermediate ring 34 with peaks and troughs in the unexpanded state, such as is depicted in FIG. 14. The troughs are connected to the peaks of the outer ring. The peaks are connected to the inner ring. The curvature of the peaks and troughs is similar between rings.

Figure 16:
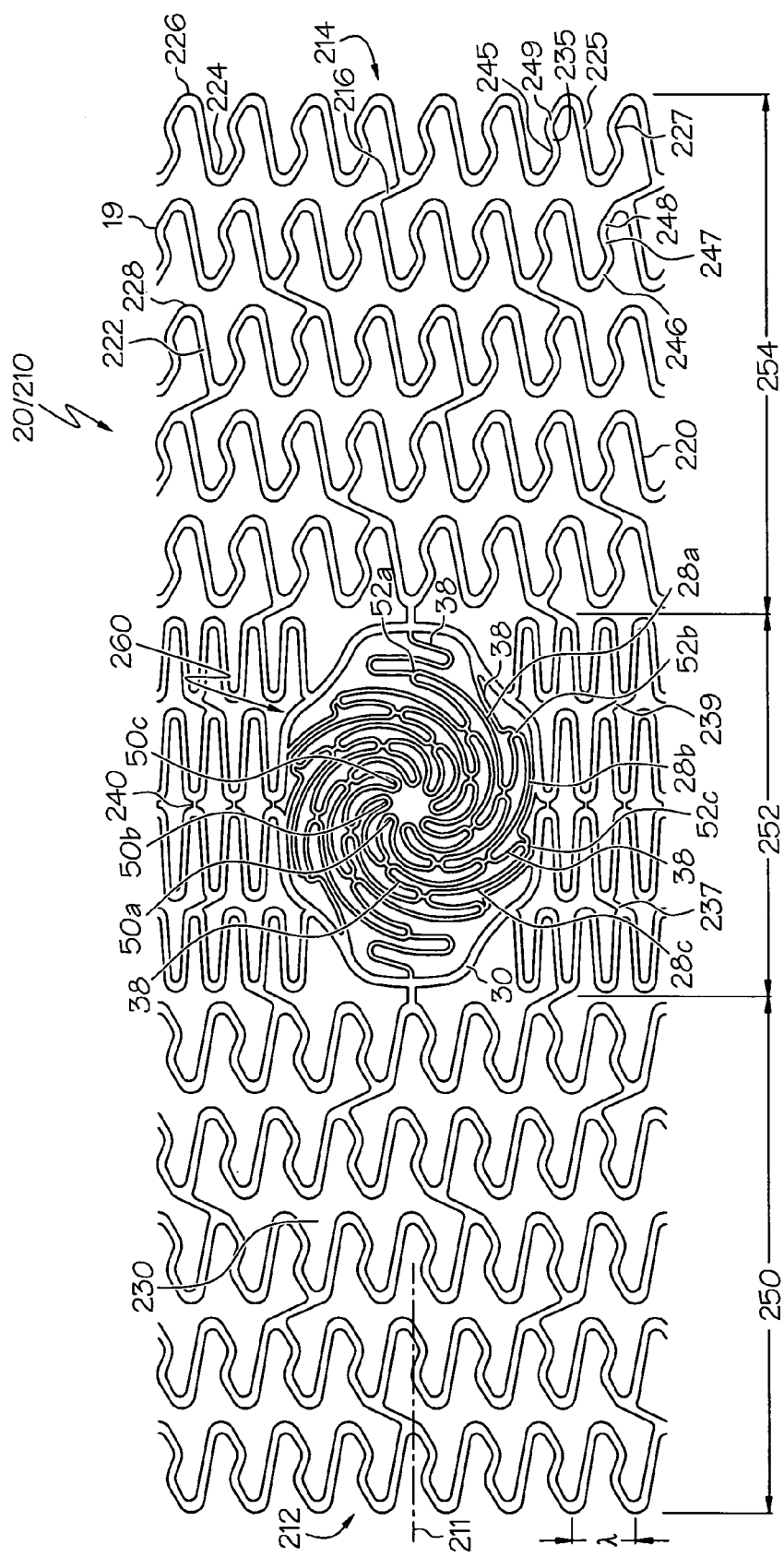
FIG. 16 is a side view of an embodiment of the stent with a spiral side branch section that has a plurality of interconnected spiral arms in an unexpanded state.

In some embodiments, the invention is also directed to a stent having a side branch section 24 with a plurality of interconnected spiral arms that extend in a pinwheel fashion around a center point, as shown by way of example in FIG. 16. The spiral side branch section 24 has an outer support member 30, a plurality of spiral arms 28, each spiral arm having a distal end 50 and a proximal end 52 and a plurality of connectors 38. The plurality of connectors 38 engage the proximal ends 52 of the spiral arms 28 to the outer support member 30 and the plurality of connectors 38 interconnect the spiral arms 28 at a plurality of locations. In this embodiment there are eight spiral arms 28, however there can be more than eight spiral arms 28.

Figure 17:
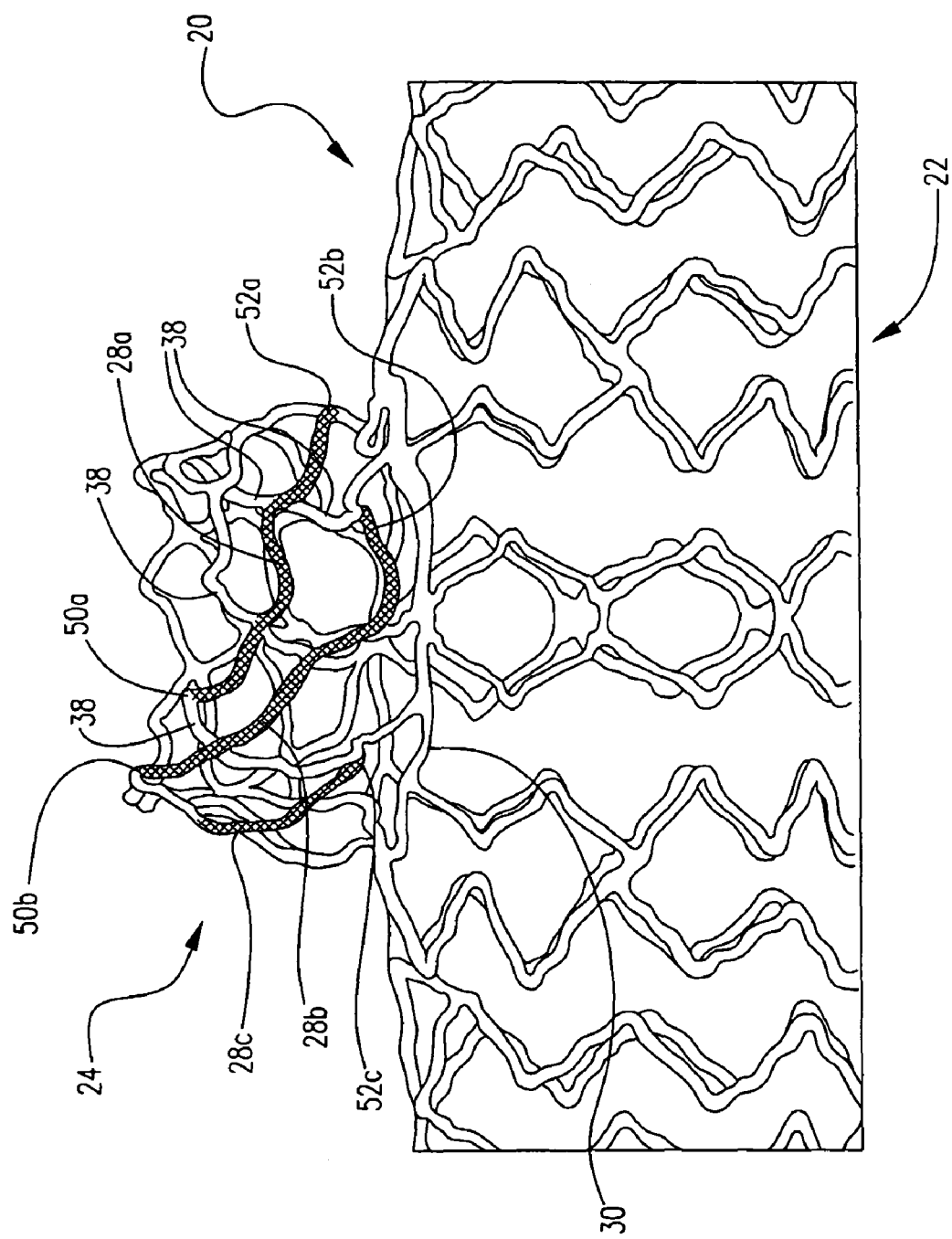
FIG. 17 is a perspective view of the embodiment in FIG. 16 in an expanded state.

FIG. 17 shows the spiral side branch embodiment of FIG. 16 in an expanded state.

Figure 8A:
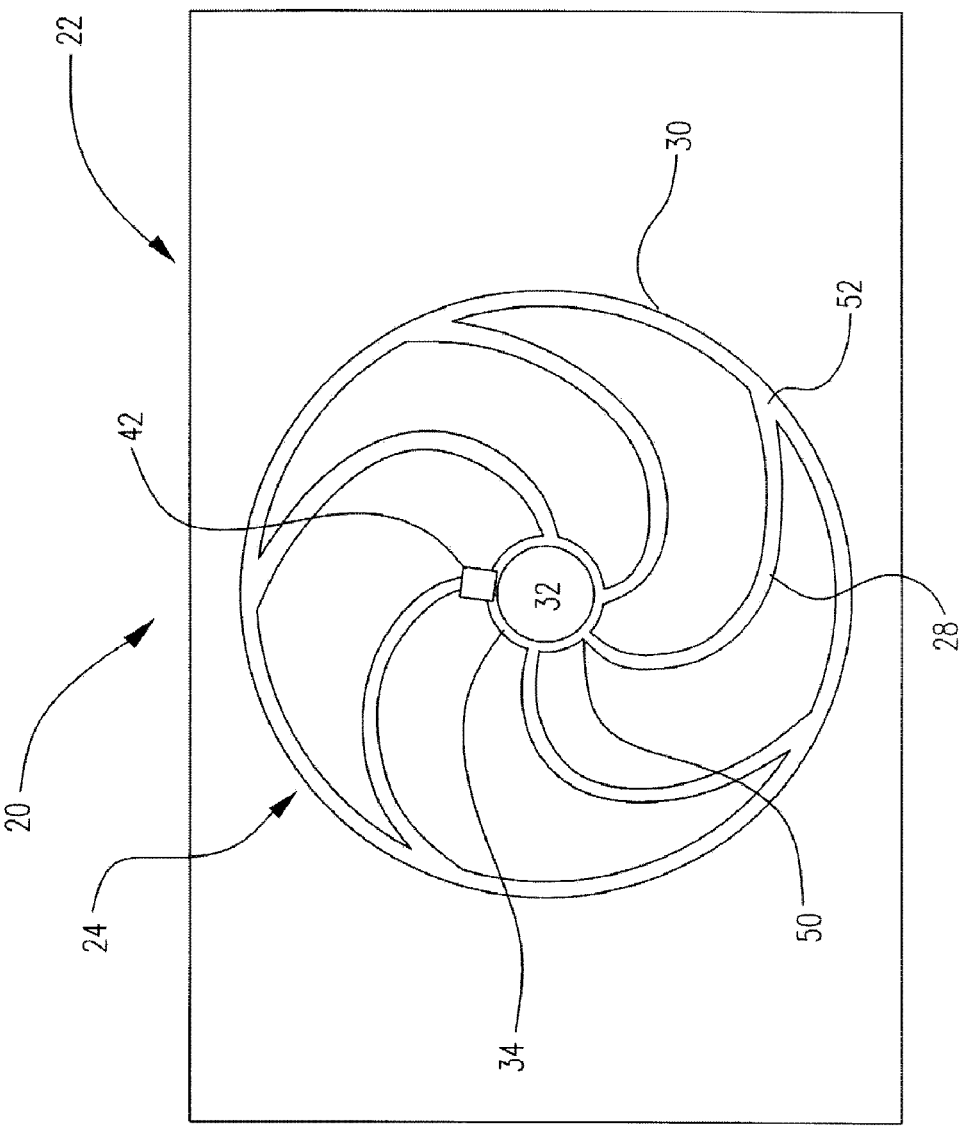
FIG. 8a is a side view of the stent with a spiral side branch section that has a circumferential member with a locking mechanism and a plurality of spiral arms in an unexpanded state.
Figure 8B:
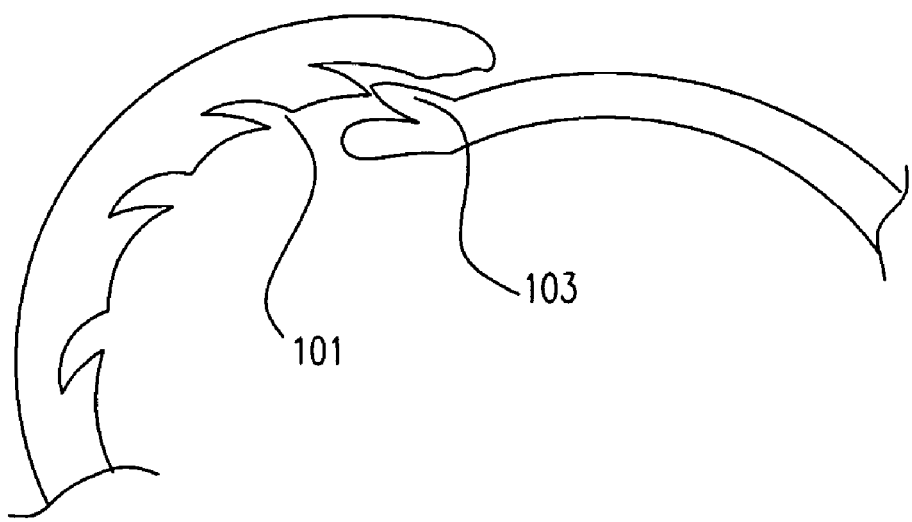
Figure 8C:
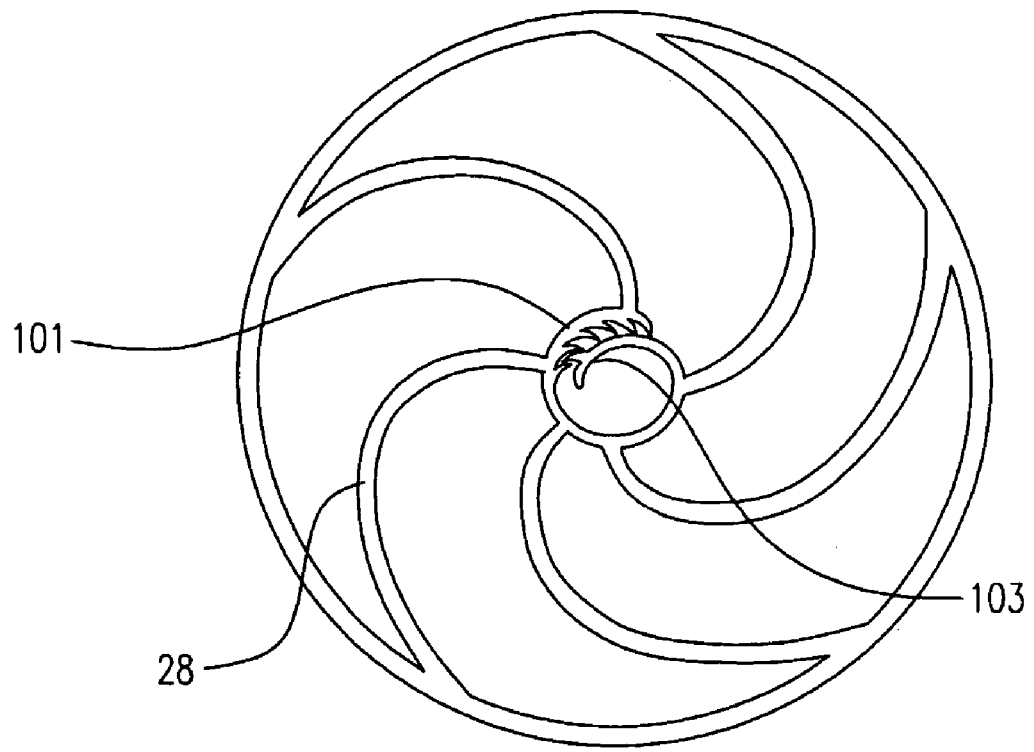
FIG. 8c shows the locking mechanism of FIG. 8b immediately prior to engagement

In the embodiment of FIG. 8*a*, the primary branch section 22 and the spiral side branch section 24 are shown in an unexpanded state. The spiral side branch section 24 has an outer support member 30, a plurality of spiral arms 28, each spiral arm having a distal end 50 and a proximal end 52, a circumferential member 34 and a locking mechanism 42. The circumferential member 34 has a first diameter 58 in an unexpanded state. The first diameter 58 is smaller than the diameter of the circumferential member 34 in an expanded state. The locking mechanism 42 only allows the circumferential member 34 to open in one direction. An example of a suitable locking mechanism is shown by way of example in FIG. 8*b*. FIG. 8*b* shows a tongue 103 and groove 101 mechanism. The mechanism is shown in FIG. 8*c* immediately prior to engagement.

Figure 9:
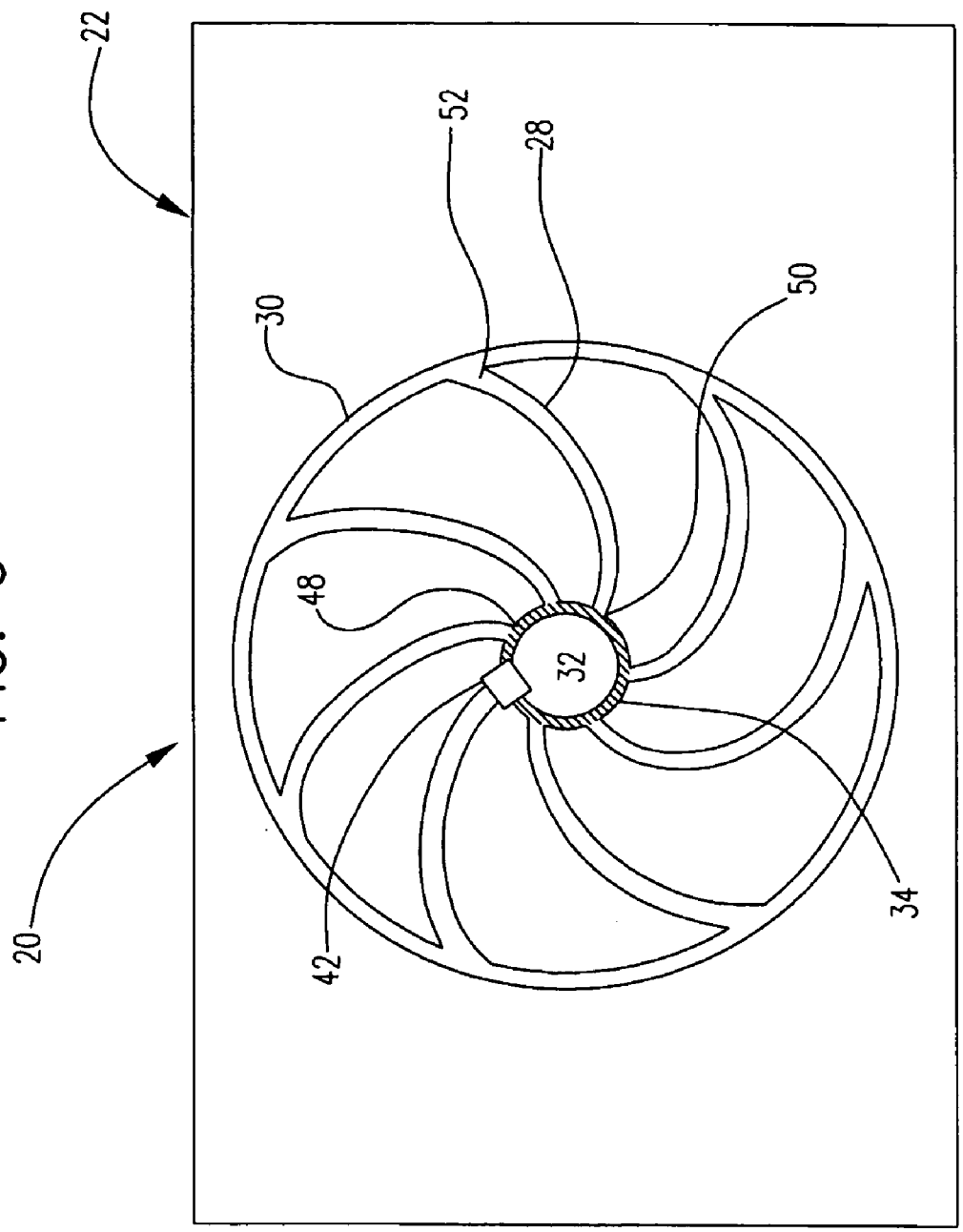
FIG. 9 is a side view of the stent in FIG. 8a with a radiopaque marker on the circumferential member.

In the embodiment of FIG. 9, the primary branch section 22 and the spiral side branch section 24 are shown in an unexpanded state. The circumferential member 34 of the spiral side branch section 24 of FIG. 8*a* has a radiopaque marker 48. The radiopaque marker 48 allows a practitioner to advance the stent 20 to the bifurcation 10 and visually align the spiral side branch section 24 of the stent 20 with the branch vessel 14 using fluoroscopy or other means. The radiopaque marker 48 may be comprise any suitable radiopaque material.

In some embodiments, the invention is also directed to a bifurcated stent having a main branch and a side branch extending from the main branch. The side branch includes a lock. The lock may be configured to lock the side branch in an expanded configuration.

In some embodiments, the invention is also directed to a stent having a sidewall with an iris-shaped structure. Examples of such are shown in FIGS. 3-9 where the side branch section 24 forms the iris shaped structure. In some embodiments, the iris-shaped structure will be present in the unexpanded state of the stent. The iris-shaped structure will desirably be expandable outward to form a side branch having a flow path therethrough, the side branch extending outward from a main flow path of the stent. The iris-shaped structure may optionally comprise a plurality of curved members such as the spiral arms disclosed above which together form a spiral pattern about a center point. In some embodiments, the curved members will be of equal length and/or shape.

In some embodiments, the curved members will have free ends. This is shown by way of example in FIG. 5. Curved members in the form of spiral arms 28 have one free end.

In other embodiments, one end of the curved arms will extend from an outer ring-like pathway and the other end of the curved arms will extend from an inner ring. An example of such a structure is shown in FIG. 3. The inner ring structure is in the form of circumferential member 34 which is a 5 pointed star while the outer ring structure is in the form of an outer support member 30 which is in the form of a circle. Another example of such is the stent of FIG. 6. The curved arms are attached at one end to outer support member 30 in the form of a circular structure. The curved arms are attached at the other end to a first circumferential member 34a which forms a propeller-like structure. The propeller-like structure may also be described as being a substantially circular structure with a plurality of folds extending therefrom. Stent 20 of FIG. 6 further includes a second propeller-like structure extending from the first propeller-like structure.

Figure 10A:
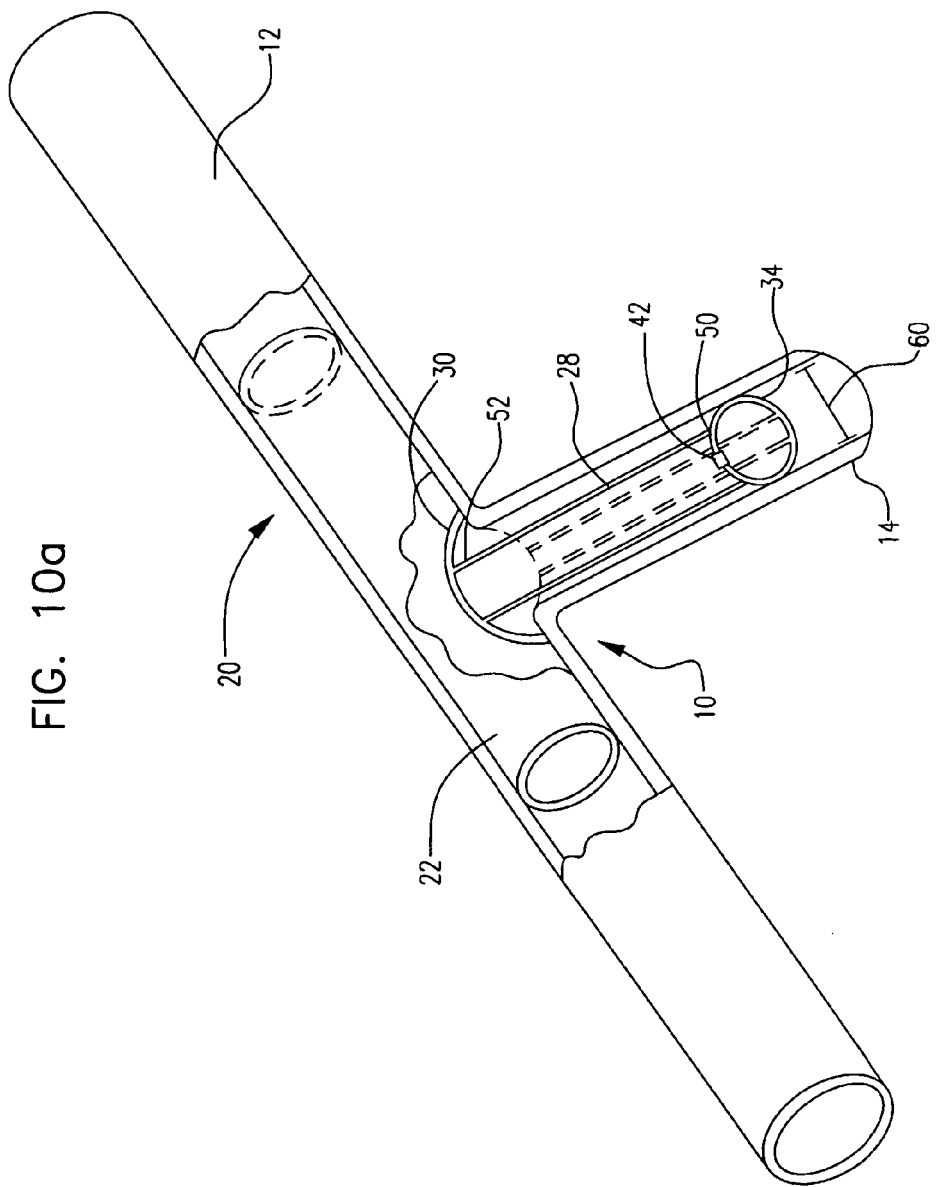
FIG. 10a is a side view of the stent of FIG. 8a with the spiral side branch section in an expanded state, the spiral arms are straight when in an expanded state.

In the embodiment of FIGS. 10a and 10b, the spiral side branch section 24 of FIG. 7 is in an expanded state. The circumferential member 34 has an expanded diameter 60. When expanded, the spiral arms 28 of the side branch section 24 either can be straight as depicted in FIG. 10a or curved as depicted in FIG. 10b.

Figure 12:
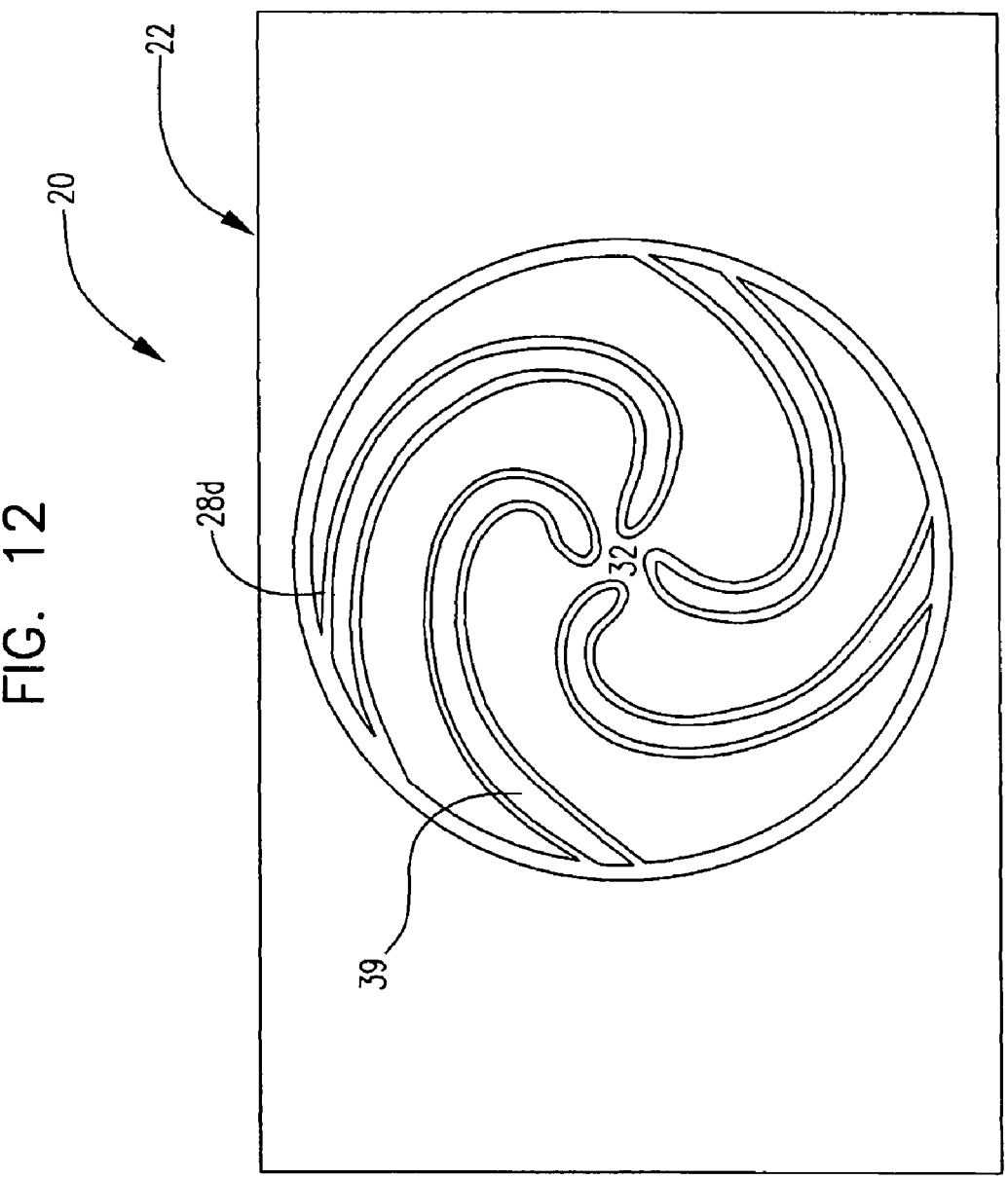
FIG. 12 is a side view of the stent with a spiral side branch section that has four spiral arms, each spiral arm having an opening in the width of the spiral arm, in an unexpanded state.
Figure 13:
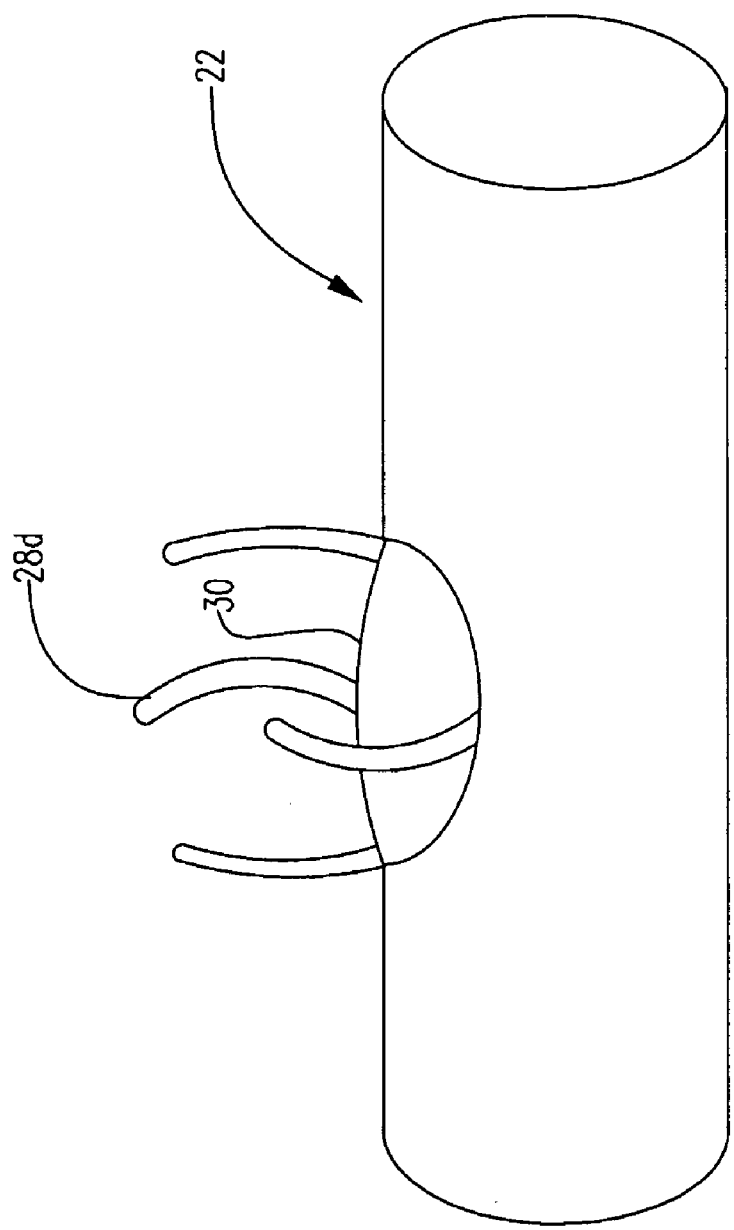
FIG. 13 is a side view of the stent with the spiral side branch section of FIG. 11 in an expanded state.

In the embodiment of FIG. 11, the primary branch section 22 and the spiral side branch section 24 are shown in an unexpanded state. The spiral side branch section 24 has an outer support member 30 and a plurality of spiral arms 28d. The spiral arms 28d have a width, length and proximal end 52. The embodiment shown in FIG. 11 has four spiral arms 28d. The spiral arms 28d can have any length. In this embodiment, all the spiral arms 28d in a spiral side branch section 24 will have the same length. In at least one embodiment, all the spiral arms 28d are not the same length. In FIG. 11, the width of the spiral arms 28d is solid. In another embodiment as shown in FIG. 12, the interior portion of the width of the spiral arm 28d may have an opening 39 therethrough. In FIG. 13, the spiral side branch section 24 of FIG. 11 is in an expanded state.

Figure 18:
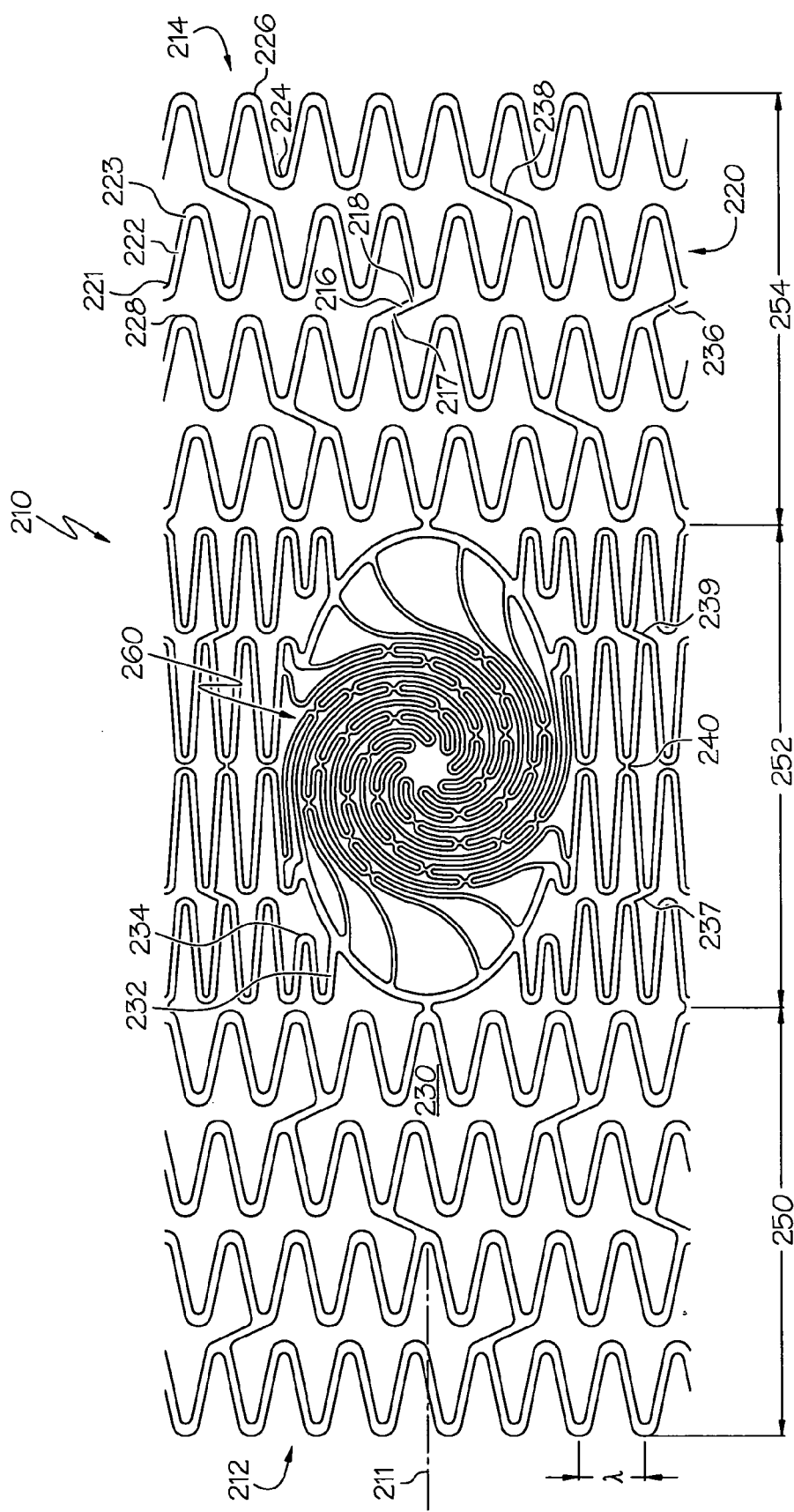
FIG. 18 shows a flat pattern for an embodiment of a stent.

FIG. 18 shows a flat pattern for another embodiment of a stent 210. In some embodiments, a sent comprises a proximal end 212, a distal end 214 and a plurality of serpentine bands 220. Each serpentine band 220 comprises a plurality of struts 222, each strut 222 having a first end 221 and a second end 223. Circumferentially adjacent struts 222 within a serpentine band 220 are connected by turns 228. Turns 228 that point toward the proximal end 212 of the stent 210 comprise proximal peaks 224, and turns 228 that point toward the distal end 214 of the stent 210 comprise distal valleys 226. Each serpentine band 220 extends about at least a portion of the stent 210 in a circumferential direction.

A stent 210 can have any suitable number of serpentine bands 220. In various embodiments, a serpentine band 220 can have any suitable number of struts 222 and any suitable number of turns 228. In some embodiments, a serpentine band 220 can have a constant wavelength λ or distance between repeating elements of the serpentine band 220. For example, a wavelength λ may comprise a distance between adjacent proximal peaks 224 of a serpentine band 220, or a distance between adjacent distal valleys 226 of a serpentine band 220. In some embodiments, the wavelength λ can change between adjacent serpentine bands 220. For example, the wavelength λ of various serpentine bands 220 may be the shortest for serpentine bands 220 located near the center of the stent 210, and may increase as the stent 210 is traversed toward either end 212, 214. In some embodiments, a serpentine band 220 may have multiple portions, where each portion comprises a different wavelength λ.

A serpentine band 220 can span any suitable distance along the length of the stent 210. In some embodiments, the proximal peaks 224 of a given serpentine band 220 can be aligned about a circumference of the stent 210, and the distal valleys 226 can be similarly aligned about another circumference of the stent 210. In some embodiments, various peaks 224 may be offset from other peaks 224 within a given serpentine band 220, and various valleys 226 may be offset from other valleys 226 within the band 220.

Each strut 222 comprises a width, which may be measured in a direction normal to the length of the strut 222. In some embodiments, all struts 222 within a given serpentine band 220 have the same width. In some embodiments, the width of various struts 222 within a serpentine band 220 may change. In some embodiments, the width of struts 222 of one serpentine band 220 can be different from the width of struts 222 of another serpentine band 220.

Each turn 228 has a width, which may be measured in a direction normal to the side of the turn 228 (e.g. normal to a tangent line). In some embodiments, the width of a turn 228 may be greater than the width of one or more struts 222 of the stent 210. In some embodiments, the width of a turn 28 may be less than the width of one or more struts 222 of the stent 210. In some embodiments, the width of a turn 228 may vary from one end of the turn 228 to the other. For example, a turn 228 may connect to a strut 222 at one end having the same width as the strut 222. The width of the turn 228 may increase, and in some embodiments may reach a maximum at a midpoint of the turn 228. The width of the turn 228 may then decrease to the width of another strut 222, which may be connected to the second end of the turn 228.

Serpentine bands 220 which are adjacent to one another along the length of the stent 210 are connected by at least one connector strut 216. In some embodiments, a connector strut 216 spans between turns 228 of adjacent serpentine bands 220. For example, a first end 217 of a connector strut 216 may connect to a distal valley 226 of one serpentine band 220, and a second end 218 of the connector strut 216 may connect to a proximal peak 224 of an adjacent serpentine band 220.

Connector struts 216 can connect to any portion of a serpentine band 220, such as a turn 228, or in some embodiments, a strut 222. In some embodiments, a connector strut 216 is linear or straight along its length. In some embodiments, a connector strut 216 can include curvature along its length, and can further include multiple portions of curvature, for example a convex portion and a concave portion that may be connected at an inflection point.

In some embodiments, a stent 210 comprises a first type of connector strut 236 and a second type of connector strut 238. A first connector strut 236 may extend in a first direction. The first connector strut 236 may be oriented at a first angle to a stent lengthwise axis 211. A second connector strut 238 may extend in a second direction that is different than or non-parallel to the first direction. In some embodiments, the first angle and the second angle may have the same magnitude but different orientations. For example, a first connector strut 236 may form a 70° angle with a stent lengthwise axis 211, while a second connector strut 238 may form a negative 70° angle with the stent lengthwise axis 211. In some embodiments, a first angle may comprise a mirror image of a second angle across a line parallel to the stent lengthwise axis 211. In some embodiments, first type of connector strut 236 can have a different shape than second type of connector strut 238.

In some embodiments, a stent 210 further comprises a third type of connector strut 237, a fourth type of connector strut 239 and a fifth type of connector strut 240. Each type of connector strut 236, 237, 238, 239, 240 may be different from each other type of connector strut 236, 237, 238, 239, 240 in at least one way, for example varying in length, width, orientation, etc. As shown in FIG. 18, in some embodiments, third connector struts 237 have an orientation similar to first connector struts 236 but have a shorter length; fourth connector struts 239 have an orientation similar to second connector struts 238 but have a shorter length; and fifth connector struts 240 comprise a connection between two longitudinally aligned turns 228.

A stent 210 further comprises a plurality of cells 230. A cell 230 comprises an opening in the wall portion of the stent 210 oriented between the expandable framework members. In some embodiments, a cell 230 may be bounded by a serpentine band 220, a connector strut 216, another serpentine band 220 and another connector strut 216.

A stent 210 comprises a first end region 250, a central region 252 and a second end region 254. Each region 250, 252, 254 extends across a portion of the length of the stent 210. Each region 250, 252, 254 includes a plurality of serpentine bands 220. In some embodiments, all of the serpentine bands 220 within a given region 250, 252, 254 are similar in size and shape. In some embodiments, various serpentine bands 220 within a given region 250, 252, 254 may be different in size, shape, strut width, wavelength λ, etc.

The central region 252 further comprises a side branch structure 260. In various embodiments, some or all of the serpentine bands 220 located in the central region 252 extend about a portion of the stent circumference, while the remainder of the circumference is occupied by the side branch structure 260.

In some embodiments, serpentine bands 220 located in the central region 252 span a greater distance along the length of the stent 210 than serpentine bands 220 located in the end regions 250, 254. In some embodiments, the struts 222 of serpentine bands 220 located in the central region 252 have a greater length than struts 222 located in the end regions 250, 254. In some embodiments, the struts 222 of serpentine bands 220 located in the end regions 250, 254 are wider than struts 222 located in the central region 252. In some embodiments, the wavelength λ of serpentine bands 220 located in the central region 252 is less than the wavelength λ of serpentine bands 220 located in the end regions 250, 254.

In some embodiments, serpentine bands 220 located in the central region 252 attach directly to a portion of the side branch structure 260. In some embodiments, a serpentine band 220 comprises one or more shorter struts 232. A shorter strut 232 is generally shorter than other struts 222 of the serpentine band 220. Shorter struts 232 may be located in proximity to the side branch structure 260, and in some embodiments, a shorter strut 232 connects to a portion of the side branch structure 260. A serpentine band 220 may also comprise one or more offset turns 234, which may connect to one or more shorter struts 232. An offset turn 234 is generally offset from other turns 228 of the serpentine band 220 that face the same direction. For example, most of the distal valleys 226 of a serpentine band 220 may be aligned about a reference circumference of the stent 210, while an offset distal valley 234 located in the same serpentine band 220 is not aligned on the aforementioned reference circumference.

Figure 19:
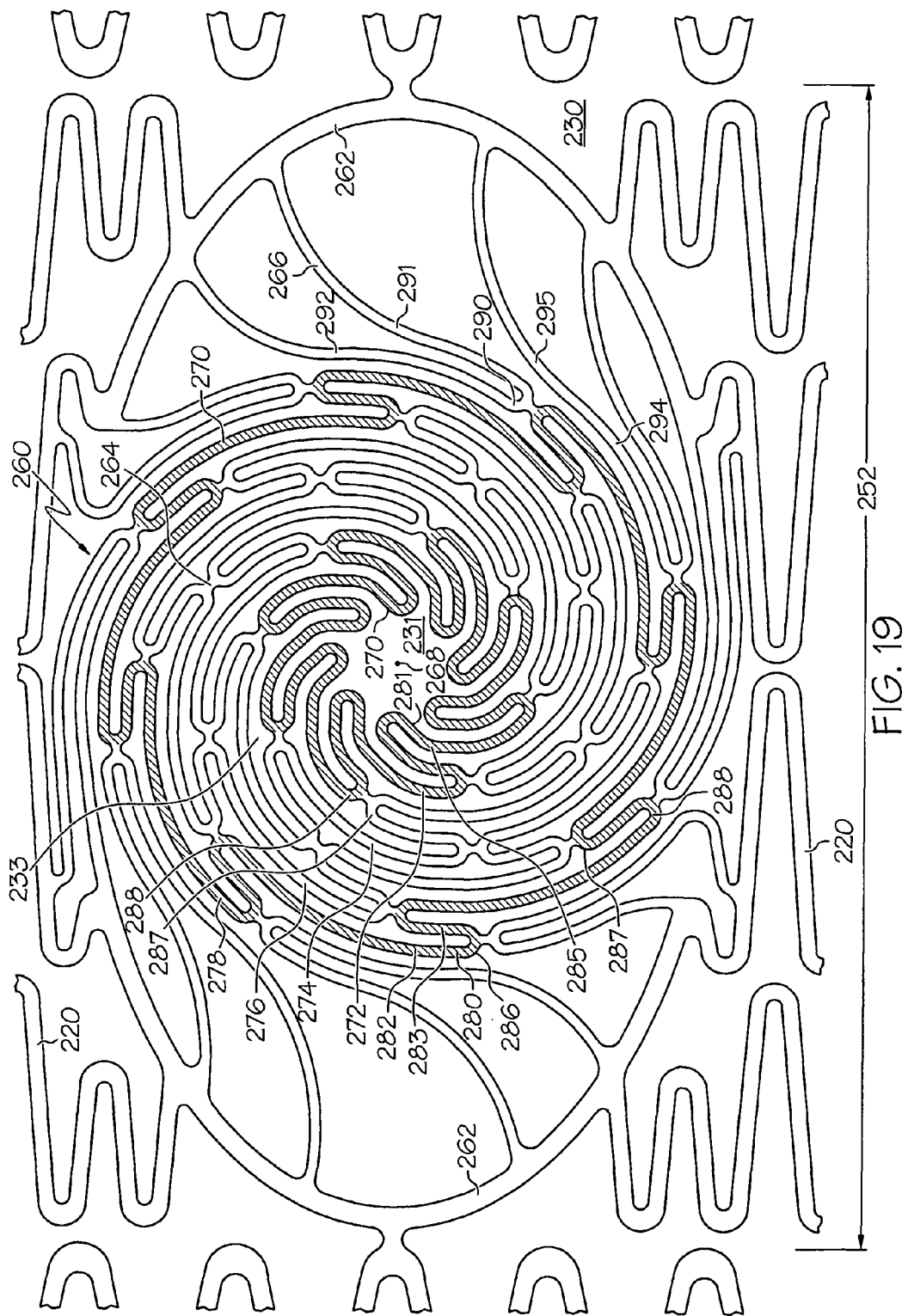
FIG. 19 shows a portion of the stent pattern of FIG. 18 in greater detail.

FIG. 19 shows the side branch structure 260 from the embodiment of FIG. 18 in greater detail. The side branch structure 260 comprises a plurality of side branch rings 270, a plurality of side branch outer connectors 266 and a plurality of side branch inner connections 264.

In some embodiments, the side branch structure 260 further comprises a plurality of outer support struts 262. In some embodiments, the outer support struts 262 are parabolic in shape and are concave with respect to the side branch center point 268. In various embodiments, the outer support struts 262 may be considered a part of the side branch structure 260, or may alternatively be considered a part of the stent 210 framework outside of the side branch structure 260.

In some embodiments, each serpentine band 220 that is located in the central region 252 that extends about only a portion of the stent 210 circumference is connected to an outer support strut 262. In some embodiments, the serpentine bands 220 are connected at one end to an outer support strut 262 at a first location and connected at the other end to the same outer support strut 262 at a different location. In some embodiments, an outer support strut 262 is further connected to a serpentine band 220 located in the first end region 250 or the second end region 254.

The side branch structure 260 can include any suitable number of side branch rings 270. In some embodiments, the multiple side branch rings 270 are concentric, with each successive side branch ring 270 oriented around the previous side branch ring(s) 270 and centered upon the side branch center point 268.

Each side branch ring 270 comprises a serpentine ring structure that is generally centered on the side branch center point 268. FIG. 19 shows a shaded inner serpentine ring 272 and a shaded outer serpentine ring 278. FIG. 19 also shows a first intermediate serpentine ring 274 and a second intermediate side branch ring 276. The innermost side branch ring 272 defines an inner side branch cell 231 that is shaped different from other cells 230 of the stent. Side branch cells 233 are further located between structural members of the side branch structure 260. In some embodiments, a side branch cell 233 comprises a curved, elongate cell, for example when located between side branch rings 270.

Each side branch ring 270 comprises alternating struts 280 and turns 286. A side branch ring 270 may comprise any suitable number of struts 280 and turns 286. In the embodiment of FIG. 19, each side branch ring 270 comprises sixteen struts 280 and sixteen turns 286.

Each strut 280 includes curvature along its length. Each strut is oriented such that at least a portion of the curvature is concave with respect to the side branch center point 268. In some embodiments, the degree of curvature is constant along the length of the strut 280. In some embodiments, a strut 280 includes at least one straight portion 281 and at least one curved portion 285. In some embodiments, the struts 280 further comprise alternating longer struts 282 and shorter struts 283.

Each turn 286 of a side branch ring 270 includes curvature along its length. In some embodiments, the turns 286 generally comprise a higher degree of curvature than the struts 280.

In some embodiments, the side branch structure 260 comprises an inner serpentine ring 272 and an outer serpentine ring 278. The longer struts 282 of the outer serpentine ring 278 are longer than the longer struts 282 of the inner serpentine ring 272. The shorter struts 283 of the outer serpentine ring 278 are shorter than the shorter struts 283 of the inner serpentine ring 272.

The turns 286 of a side branch ring 270 further comprise alternating inner turns 287 and outer turns 288. The inner turns 287 are located closer to the side branch center point 268 than the outer turns 288. In some embodiments, each inner turn 287 of a side branch ring 270 is located an equal distance away from the side branch center point 268, and the inner turns 287 may further be equally spaced around the side branch center point 268. Similarly, in some embodiments, each outer turn 288 of a side branch ring 270 is located an equal distance away from the side branch center point 268, and the outer turns 288 may further be equally spaced around the side branch center point 268.

The outer turns 288 of one side branch ring 270 may be connected to the inner turns 287 of another side branch ring 270. For example, the outer turns 288 a first side branch ring 272 may be connected to the inner turns 287 of a second side branch ring 274. In some embodiments, an outer turn 288 of one side branch ring 270 is connected to an inner turn 287 of another side branch ring 270 via a side branch inner connection 264.

In some embodiments, the side branch inner connections 264 are very short and may be considered a direct connection between turns 286 of the side branch rings 270. In some embodiments, a side branch inner connection 264 comprises a short strut, for example having a length that is less than or equal to its width.

In some embodiments, the multiple side branch rings 270 form a spiral pattern that extends around the inner side branch cell 231.

The side branch rings 270 are connected to other portions of the stent 10 framework by a plurality of side branch outer connectors 266. Each side branch outer connector 266 spans between a turn 286 of a side branch ring 270 and another portion of the stent 210, such as side branch outer support strut 262 or a portion of a serpentine band 220.

In some embodiments, a side branch outer connector 266 comprises a first outer connector strut 291, an outer connector turn 290 and a second outer connector strut 292. The outer connector turn 290 connects to a turn 286 of a side branch ring 270. In some embodiments, the outer connector turn 290 and the turn 286 of the side branch ring 270 are connected by a side branch inner connection 264. Each outer connector strut 291, 292 is connected at one end to the outer connector turn 290 and at the other end to another portion of the stent 210, such as a side branch outer support strut 262 or a portion of a serpentine band 220. In some embodiments of a side branch outer connector 266, the first outer connector strut 291 connects between the outer connector turn 290 and an outer support strut 262, and the second outer connector strut 292 connects between the outer connector turn 290 and a serpentine band 220.

In some embodiments, an outer connector strut 290, 291 comprises a first portion 294 that is concave with respect to the side branch center point 268, and a second portion 295 that is convex with respect to the side branch center point 268. In some embodiments, the degree of curvature of the concave portion 294 can be the same as the degree of curvature of a strut 280 of the side branch ring 270 to which the side branch outer connector 266 connects.

Figure 20:
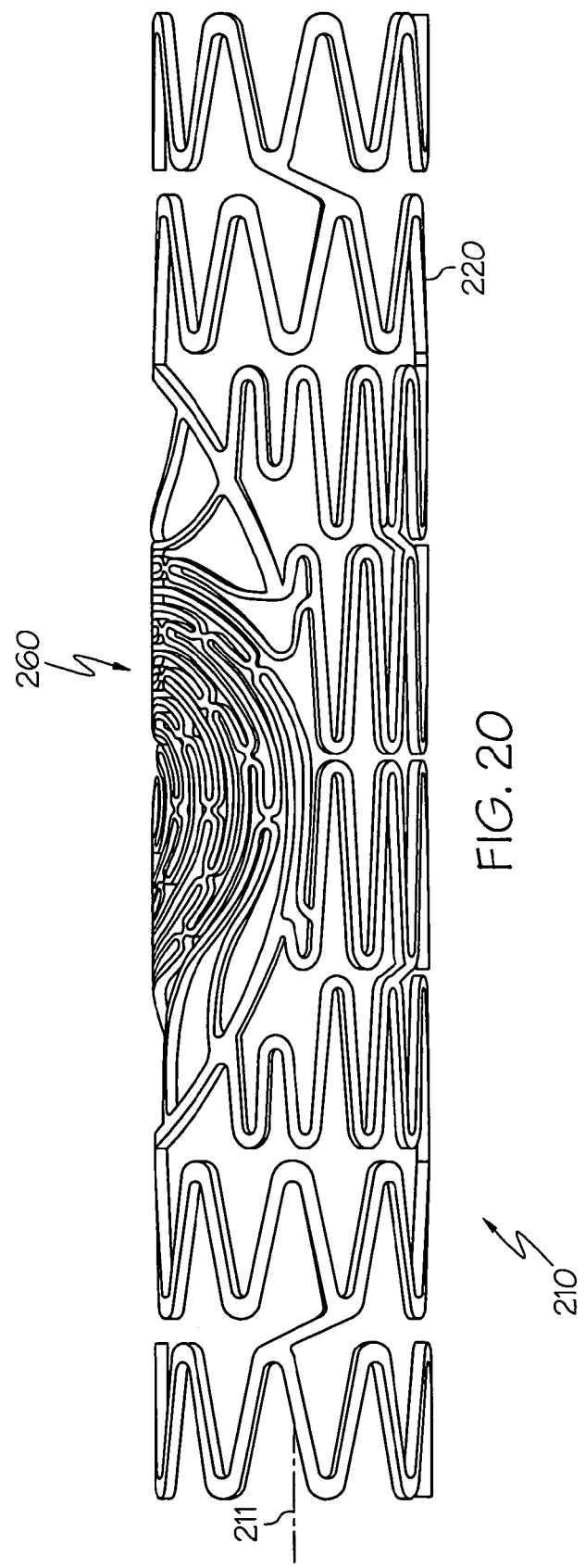
FIG. 20 shows an embodiment of a stent in a three-dimensional cylindrical configuration.

FIG. 20 depicts a three-dimensional image of a stent 210 according to the pattern of FIG. 18. The stent 210 is shown in an unexpanded state. The stent 210 may be expanded using any suitable method. In one embodiment, an inflatable balloon may be used to expand the generally cylindrical expandable framework (e.g. the serpentine bands), thereby increasing the general diameter of the stent 210. The side branch structure 260 may then be further outwardly deployed in a stent radial direction, for example by a secondary inflatable portion of the inflatable balloon.

Figure 21:
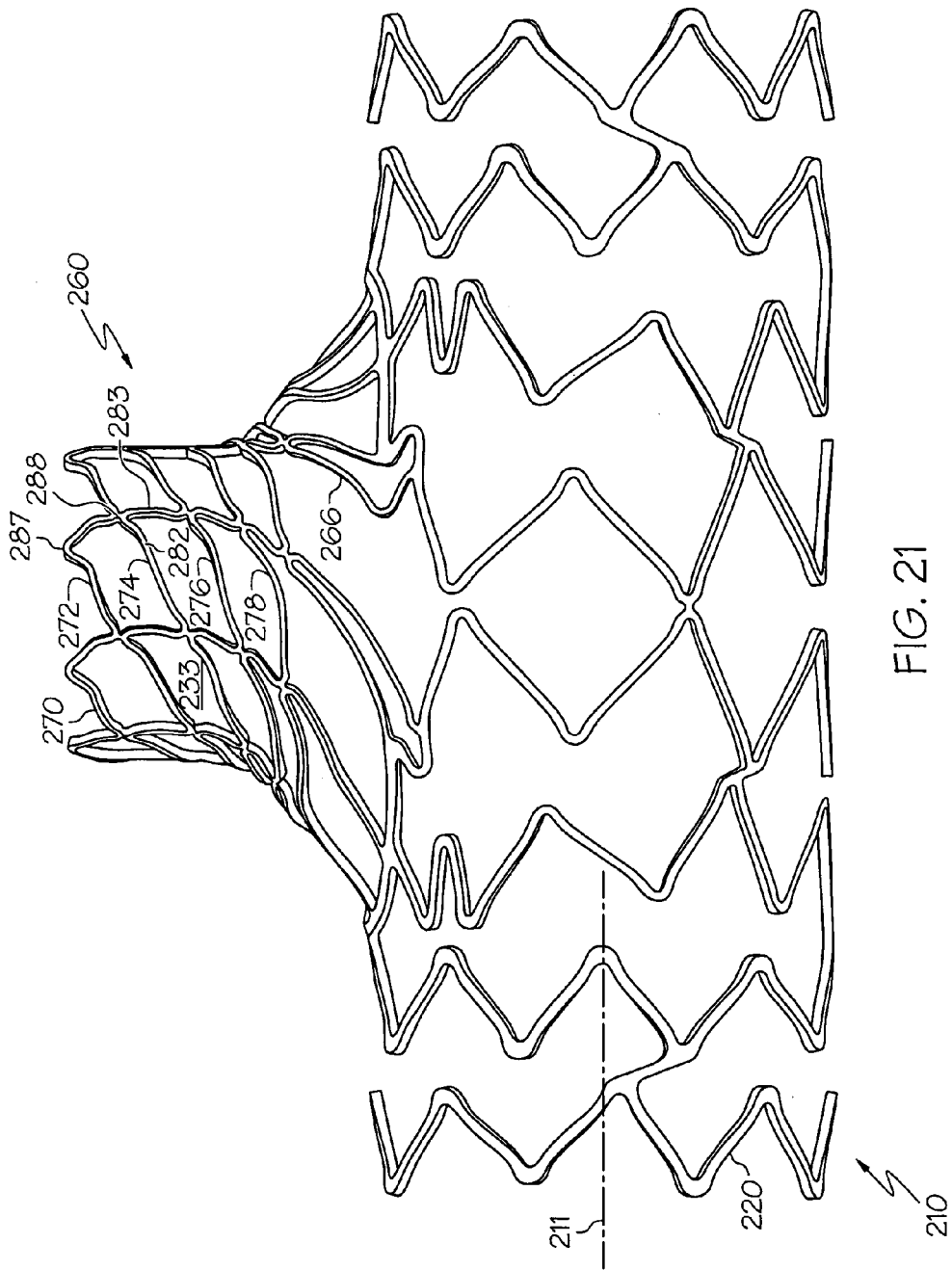
FIG. 21 shows the stent of FIG. 20 in an expanded state with the side branch structure outwardly deployed.

FIG. 21 shows the stent 210 of FIG. 20 in an expanded and deployed state. The side branch rings 270 have been deployed outwardly in a stent radial direction and have been reoriented. Each side branch ring 270 has been opened and defines a greater diameter in the deployed state than in the unexpanded state.

Upon deployment, the side branch rings 270 that are located closer to the side branch center point 268 in the unexpanded state are displaced farther outwardly. Thus, the innermost side branch ring 272 is located the farthest away from the stent longitudinal axis 211 after deployment, while the outermost side branch ring 278 is the closest side branch ring 270 to the stent longitudinal axis 211.

In the deployed state, the outer turns 288 of a side branch ring 270 are located closer to the stent longitudinal axis 211 than the inner turns 287. The side branch cells 233 generally increase in size. In some embodiments, a side branch cell 233 comprises a parallelogram shape after deployment of the side branch structure 260.

Figure 22:
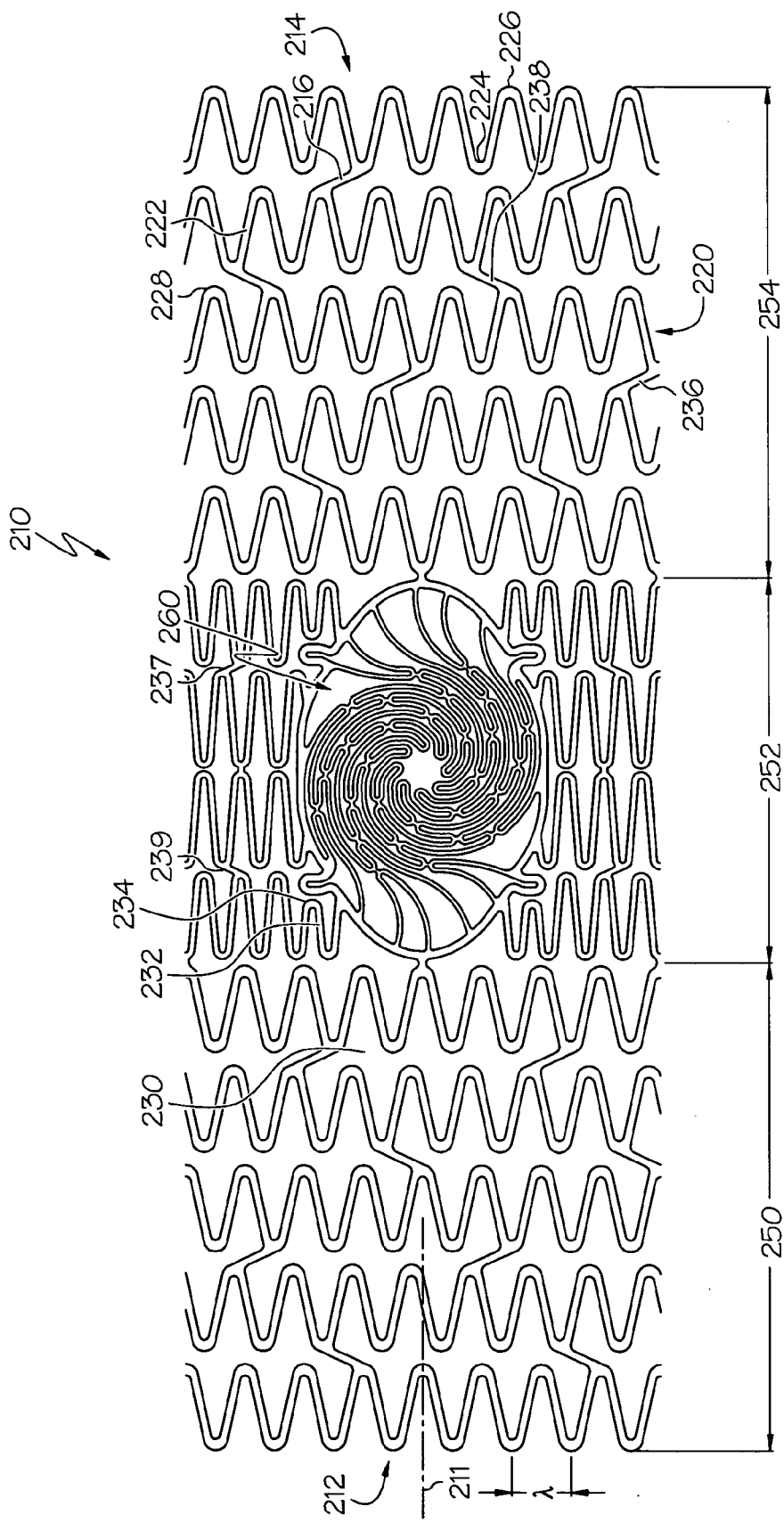
FIG. 22 shows a flat pattern for another embodiment of a stent.

FIG. 22 shows a flat pattern for another embodiment of a stent 210. The embodiment of FIG. 22 includes many of the features described with respect to the embodiment of FIG. 18, as indicated by like reference numerals.

Figure 23:
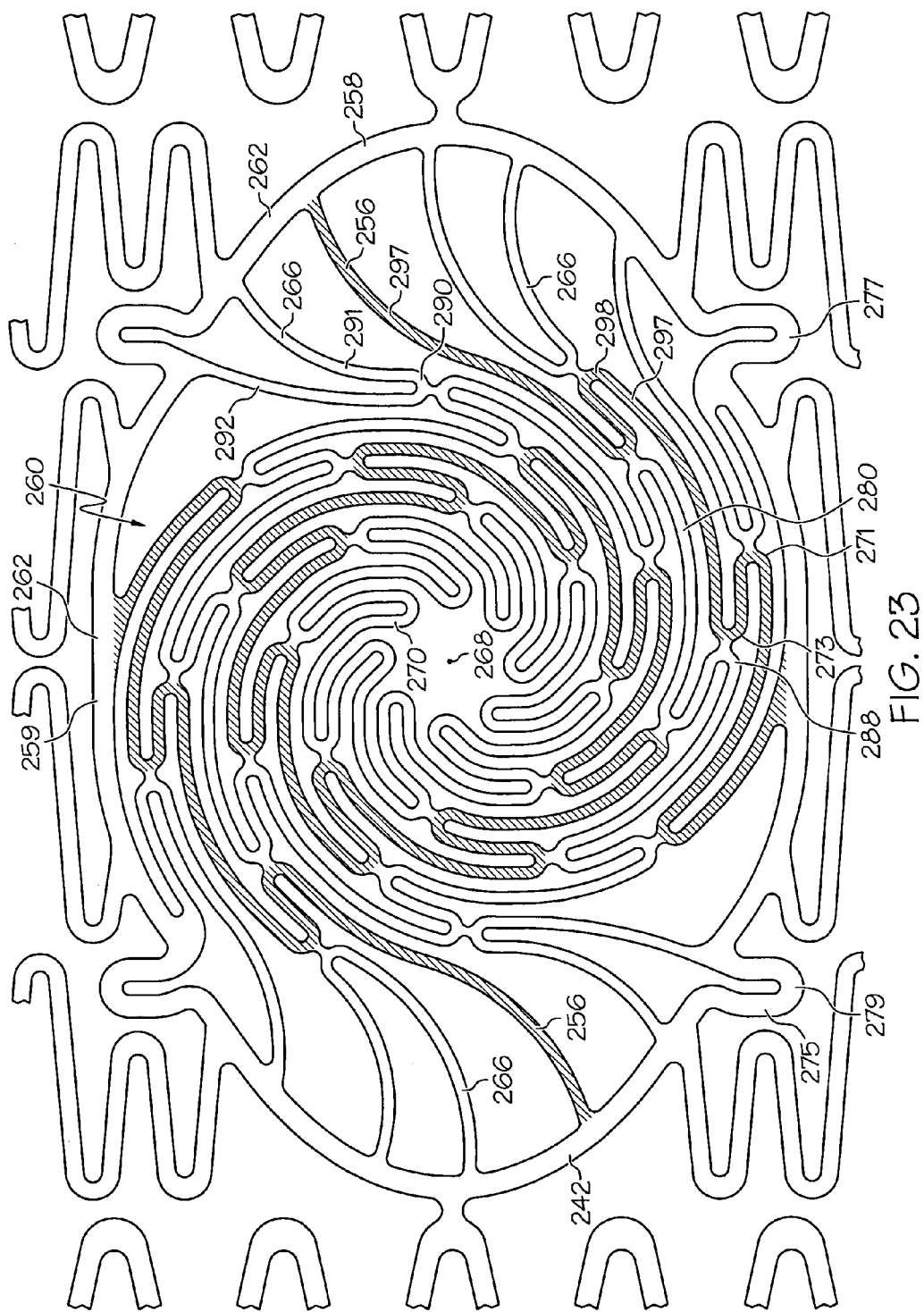
FIG. 23 shows a portion of the stent pattern of FIG. 22 in greater detail.

FIG. 23 shows the side branch structure 260 of FIG. 22 in greater detail. A continuous support ring 242 extends around the side branch rings 270 and side branch outer connectors 266. In some embodiments, the support ring 242 comprises a substantially constant strut width, and in some embodiments, struts of the support ring 242 have a greater width than elements of the serpentine bands 220 or other side branch structure 260. In some embodiments, the support ring 242 comprises a plurality of outer support struts 262. In some embodiments, an outer support strut 262 is parabolic in shape and is concave with respect to the side branch center point 268, for example as indicated by reference numeral 258. In some embodiments, an outer support strut 262 comprises a non-parabolic curved shape that is concave with respect to the side branch center point 268, for example as indicated by reference numeral 259.

The support ring 242 further comprises a plurality of loop portions 277 which provide the stent 210 with greater longitudinal flexibility. Each loop portion 277 comprises a loop turn 279 and a plurality of loop struts 275. In some embodiments, at least a portion of the length of a loop strut 275 is oriented in a stent circumferential direction. In some embodiments, a loop turn 279 is oriented with a peak (e.g. a maximum or minimum) pointed in a stent circumferential direction.

The side branch structure 260 further comprises at least one side branch serpentine connector 256. In the embodiment shown in FIG. 23, two side branch serpentine connectors 256 are shaded. Each side branch serpentine connector 256 is connected to the support ring 242 at each end. In some embodiments, a side branch serpentine connector 256 is connected at one end to a parabolic strut portion 258 and connected at the other end to a non-parabolic strut portion 259.

Each side branch serpentine connector 256 comprises a plurality of struts 297 and turns 298. In some embodiments, at least a portion of the struts 297 and turns 298 form a pattern similar to the pattern of the side branch rings 270. In some embodiments, the struts 297 comprise alternating longer struts and shorter struts. In some embodiments, a strut 297 includes curvature along its length and is concave with respect to the side branch center point 268. In some embodiments, the degree of curvature of the strut 297 can be the same as the degree of curvature of a strut 280 of a side branch ring 270 to which the side branch outer connector 266 connects.

In some embodiments, the side branch serpentine connector turns 298 comprise alternating inner turns 273 and outer turns 271. The inner turns 273 are located closer to the side branch center point 268 than the outer turns 271. In some embodiments, each inner turn 273 is located an equal distance away from the side branch center point 268, and each outer turn 271 is located an equal distance away from the side branch center point 268. In some embodiments, an inner turn 273 connects to an outer turn 288 of a side branch ring 270. In some embodiments, multiple inner turns 273 of a side branch serpentine connector 256 connect to multiple outer turns 288 of a side branch ring 270. In some embodiments, an outer turn 271 of a side branch serpentine connector 256 connects to a connector turn 290 of a side branch outer connector 266.

In some embodiments, a side branch outer connector 266 comprises a first outer connector strut 291 and a second outer connector strut 292 that connect to the support ring 242 on opposite sides of a support ring loop 277.

Figure 24:
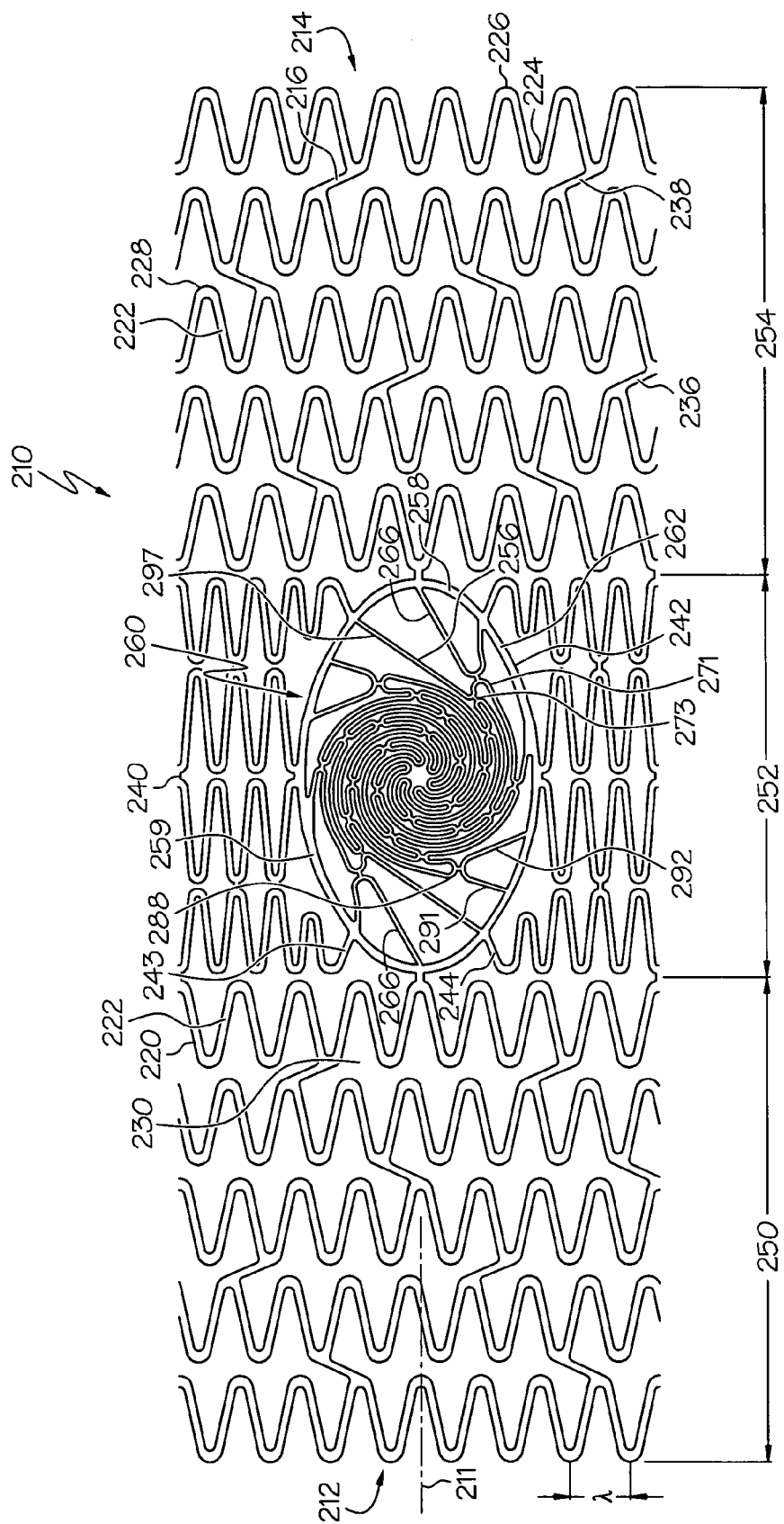
FIG. 24 shows a flat pattern for another embodiment of a stent.

FIG. 24 shows a flat pattern for another embodiment of a stent 210. The embodiment of FIG. 24 includes many of the features described with respect to previous embodiments described herein, as indicated by like reference numerals.

In some embodiments, a serpentine band 220 comprises a first nonparallel strut 243 and a second nonparallel strut 244. Each nonparallel strut 243, 244 is nonparallel to any other strut 222 of the serpentine band 220 according to the flat pattern.

The side branch structure 260 comprises a continuous support ring 242 that extends around the side branch rings 270 and side branch outer connectors 266. In some embodiments, the support ring 242 comprises a substantially constant strut width, and in some embodiments, struts of the support ring 242 have a greater width than elements of the serpentine bands 220 or other side branch structure 260.

In some embodiments, the support ring 242 comprises a structure that is continuously concave with respect to the side branch center point 268. Thus, in some embodiments, the support ring 242 does not include any portions of curvature that are convex with respect to the side branch center point 268.

In some embodiments, a side branch serpentine connector 256 comprises a strut 297 that is straight along its length. A straight strut 297 may connect at one end to the support ring 242 and at the other end to an inner turn 273 of the side branch serpentine connector 256.

In some embodiments, an outer turn 271 of a side branch serpentine connector 256 can have curvature of a lesser degree than an inner turn 273. Thus, the outer turn 271 forms an arc having a larger radius than the arc of the inner turn 273.

In some embodiments, a side branch outer connector 266 comprises a first outer connector strut 291 that is straight along its length, and a second outer connector strut 292 that is straight along its length and nonparallel to the first outer connector strut 291. A side branch outer connector 266 may further comprise a connector turn 290 that has curvature of a lesser degree than a turn to which it connects, such as an outer turn 288 of a serpentine ring 270 or an outer turn 271 of a side branch serpentine connector 256.

In some embodiments, the outer turns 288 of a side branch ring 270 that connect to an outer side branch connector 266 have curvature of a lesser degree than the outer turns 288 of the side branch ring 270 that connect to a side branch serpentine connector 256.

Referring again to FIG. 16, the embodiment includes many of the features described with respect to other embodiments described herein, for example FIGS. 18-24, as indicated by like reference numerals.

In some embodiments, the struts 222 of a serpentine band 220 may comprise straight struts 225 and/or bent struts 227. A straight or linear strut 225 is substantially straight along its length. A bent strut 227 desirably includes curvature along its length. In some embodiments, a bent strut 227 may comprise an s-shape. In some embodiments, an s-shape may comprise a first curved portion 245 and a second curved portion 249. The curvature orientation of the first curved portion 245 may be different than the curvature orientation of the second curved portion 246. For example, if the first curved portion 245 may be considered convex, the second curved portion 249 may be considered concave. An s-shaped strut 227 may include an inflection point 235 where the curvature changes orientation.

In some embodiments, an s-shape may comprise a first portion 246, a second portion 247 and a third portion 248. The first portion 246 and the third portion 248 can be parallel or substantially parallel to one another, and may extend at an angle to the stent lengthwise axis 211. The second portion 247 may be centrally located between the first portion 246 and the third portion 248, and may extend an angle to the stent lengthwise axis 211 different the first portion 246 or the third portion 248. In some embodiments, an angle between the stent lengthwise axis 211 and the first portion 246 may comprise a mirror image of an angle between the stent lengthwise axis 211 and the second portion 247, the mirror image taken across a stent circumferential line.

In some embodiments, a serpentine band 220 comprises alternating straight struts 225 and bent or s-shaped struts 227. Each straight strut 225 may be oriented between two bent struts 227. Thus, a first end of a straight strut 225 may be connected to a proximal peak 224 which may connect to a bent strut 227 located on one side of the straight strut 225. A second end of the straight strut 225 may be connected to a distal valley 226 which may connect to another bent strut 227 located on the other side of the straight strut 225. Similarly, each bent strut 227 may be oriented between two straight struts 225.

Figure 25:
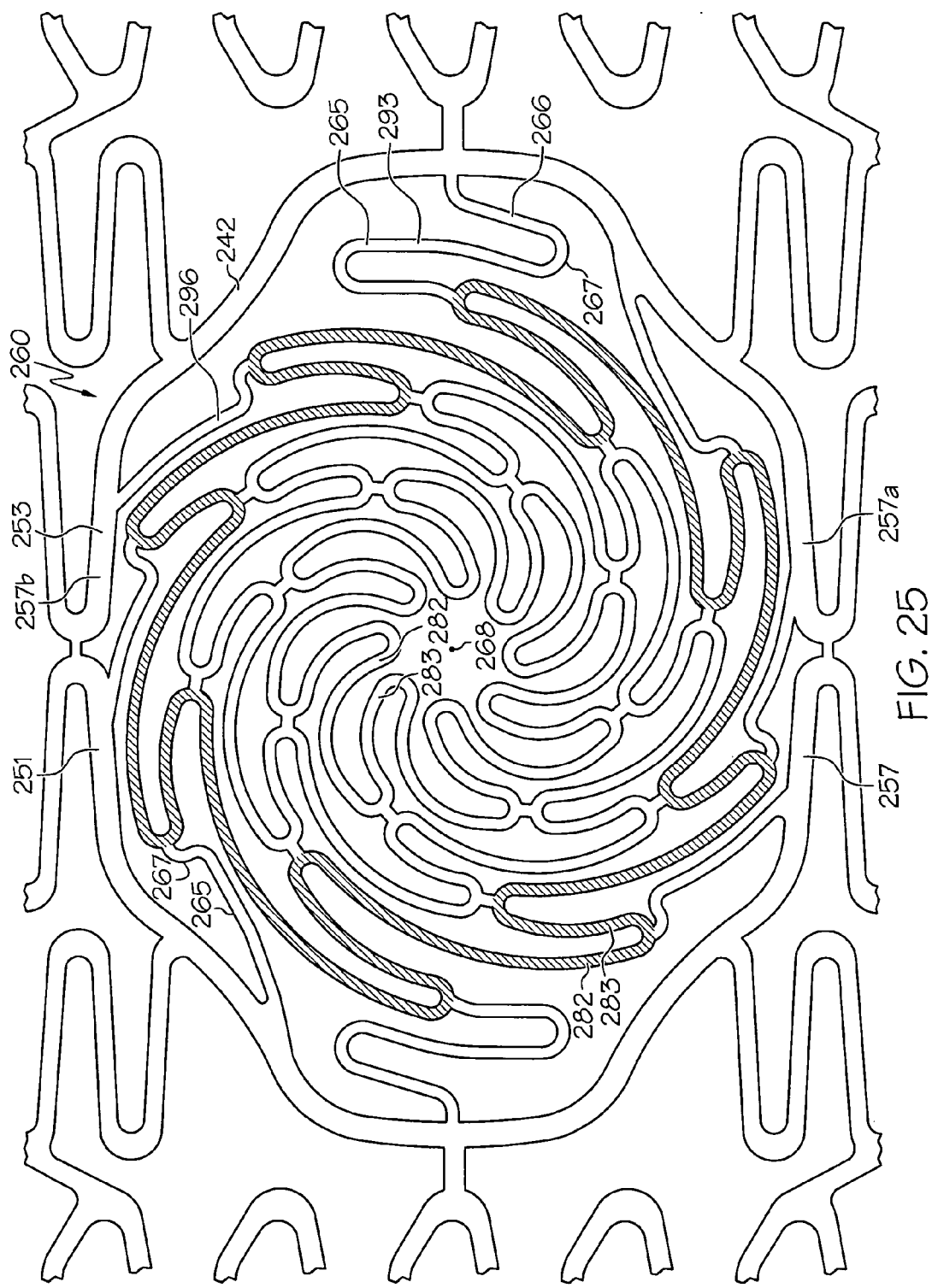
FIG. 25 shows a portion of the stent pattern of FIG. 16 in greater detail.

FIG. 25 shows the side branch structure 260 of the embodiment of FIG. 16 in greater detail. A side branch ring 270 may comprise alternating longer struts 282 and shorter struts 283. In some embodiments, a longer strut 282 includes curvature of a higher degree than a shorter strut 283. Thus, the longer strut 282 forms an arc having a smaller radius than an arc formed by the shorter strut 283.

In some embodiments, the support ring 242 comprises a first portion 251 and a second portion 253. Each portion comprises a continuous strut having a width that is greater than the width of other elements of the stent 210. In some embodiments, the first portion 251 comprises a mirror image of the second portion 253 taken across a circumference of the stent that intersects the side branch center point 268.

In some embodiments, each portion 251, 253 comprises at least one continuation strut 257 that comprises a continuation of a serpentine band 220. A continuation strut 257 is connected at one end to another portion of the support ring 242, and is connected at the other end to a turn 228 of a serpentine band 220. Thus, the serpentine band 220 transitions into the continuation strut 257 of the support ring 242. Each continuation strut 257 may be substantially straight along its length, and may be oriented parallel to a plurality of struts 222 of the serpentine band 220 to which it connects. In some embodiments, a portion 251, 253 comprises a first continuation strut 257a and a second continuation strut 257b. The first continuation strut 257a is parallel to a first plurality of struts 222 of the serpentine band 220. The second continuation strut 257b is parallel to a second plurality of struts 222 of the serpentine band 220. The first continuation strut 257a is further nonparallel to the second continuation strut 257b.

In some embodiments, a side branch outer connector 266 comprises an s-shape and includes at least one strut 265 and a plurality of turns 267. In some embodiments, a first outer side branch connector 293 comprises an s-shape formed by at least one strut 265 and two turns 267, wherein the strut 265 is located between the turns 267. In some embodiments, a second outer side branch connector 296 comprises an s-shape formed by two turns 267, wherein the turns 267 are connected to one another.

The turns 267 of a first outer side branch connector 293 may have a larger radius than the turns 267 of a second outer side branch connector 296. Thus, a first outer side branch connector 293 may be used in areas where a greater amount of scaffolding support is desirable for a vessel. In the embodiment of FIG. 25, second outer side branch connectors 296 are used in a central longitudinal region of the side branch structure 260, and first outer side branch connectors 293 are used at the longitudinal extremities of the side branch structure 260. Thus, upon expansion of the stent 210 and deployment of the side branch structure 260, the first outer side branch connectors 293 are positioned to provide scaffolding support to the carina and contralateral ostial wall portions of a vessel bifurcation.

In yet another embodiment of the invention, a stent may be provided with a side branch support section with one or more self-expandable members extending therefrom. The self-expandable member may be in the form of a shape memory wire whose memorized shape is that of a coil. Any suitable shape memory material may be used including nitinol. The wire may be coiled when in the martensitic state and straightened and projecting outward in the austenitic state with a transition temperature at or below body temperature. The stent may be maintained in its straightened shape via a sheath. Once the one or more wires are in the bifurcated vessel, upon removal of the sheath, the one or more wires may assume the form of a coil. The wires may be welded to the main body of the stent or otherwise suitably attached thereto. It is within the scope of the invention to include only one such wire per side branch to be formed or to include two, three, four, five or more wires per side branch location.

In another embodiment of the invention, the self-expanding wires need not be attached to the main body of the stent. Rather, the one or more wires may be delivered to the desired bodily location once a primary stent, optionally balloon expandable, has been delivered to the desired bodily location. The delivery of the one or more wires to the side branch may also be simultaneous with the delivery of the primary stent. Where two wires which form coils are to be used, the wires may be arranged such that they form counter-wound helices.

Any of the inventive stents disclosed herein may have a uniform inner diameter and/or a uniform outer diameter in the unexpanded state and/or in an expanded state. The inventive stents disclosed herein may also be provided in an embodiment in which the inner and/or outer diameters are not uniform. For example, one or more portions of the stent may have a tapered outer diameter. The main body may be tapered, the side branch may be tapered or both may be tapered.

In any of the inventive stents disclosed herein, the spiral side branch section may have one or more spiral arms. The spiral side branch may be of uniform diameter when expanded or variable diameter when expanded. As an example of the latter, the spiral side branch, when expanded, may have a portion which tapers. The spiral side branch may taper from a larger diameter at the bifurcation to a smaller diameter further into the bifurcation vessel.

In many of the embodiments shown in the figures, there is no more than one spiral branch support section located in a given circumferential section of the stent. In other embodiments of the invention, additional spiral branch support sections may be located within a given circumferential segment of the stent. The inventive stents may also have multiple spiral branch support sections disposed along the length of the stent.

Also, in many of the figures, portions of the inventive stent are drawn without showing structure. It is understood that any suitable structure may be employed including, but not limited to, the cellular patterns, shown by way of example only, in U.S. Pat. Nos. 6,835,203, 6,348,065, and 6,013,091.

At least some of the embodiments disclosed herein, for example, that of FIG. 1, are advantageous in that they do not require the spiral arms to be bent back at angles in excess of 90 degrees when the side branch is expanded. Many of the prior art bifurcated stents which have petals will include petals which are bent back in excess of 90 degrees when the side branch is deployed.

At least some of the embodiments, for example, at least that of FIG. 1, are advantageous in that, for a given length of starting material (for example, a tubular blank), a longer side branch section can be made via the use of spirals.

In at least one embodiment, the invention is directed to a stent that has an expandable primary branch section and a separately expandable spiral side branch section that forms a part of the primary branch section. The expandable primary branch section is a substantially tubular body disposed about a longitudinal axis. The expandable primary branch section has a first diameter in an unexpanded state and a second diameter in an expanded state. The spiral side branch section has an unexpanded state and an expanded state. In an unexpanded state the entirety of the spiral side branch section forms a part of the surface of the substantially tubular body of the primary branch section. Thus, the spiral side branch section has the same uniform thickness as the primary branch section. The spiral side branch section has an outer support member and at least one spiral arm that curves around an opening in the spiral side branch section. The outer support member can have any shape, e.g. a shape that corresponds to the cellular design of the primary stent section, a circular shape or a serpentine shape. Each spiral arm has a proximal end and a distal end. The distal end of the spiral arm is positioned closer to the center of the opening of the spiral side branch support section than the proximal end. A non-bifurcated stent is formed when the primary branch section is in an expanded state and the spiral side branch section is in an unexpanded state. A bifurcated stent is formed when both the primary branch section and the spiral side branch section are in an expanded state.

In at least one embodiment, the spiral side branch section has only one spiral arm that expands into a coil when the spiral side branch section is in an expanded state.

In at least one embodiment, the spiral side branch section has a plurality of spiral arms. The distal ends of the spiral arms expand into a helix or multiple helices when the spiral side branch section is in an expanded state. The spiral design provides uniform support and a custom fit for tapering vessels.

In at least one embodiment, the spiral side branch section has a plurality of spiral arms and a circumferential member. The circumferential member has a first diameter in an unexpanded state and second diameter in an expanded state, the second diameter is larger than the first diameter. A plurality of spiral arms is engaged to the circumferential member. The circumferential member can be any shape. Some shapes, such as a star, can have apexes and valleys. If the shape has apexes and valleys, the spiral arms can be engaged to the circumferential member at the apexes, at the valleys, or anywhere in between. The circumferential member provides support at the distal end of the spiral side branch section.

In another embodiment the circumferential member has a serpentine shape, which has turns. In one embodiment the plurality of spiral arms are engaged to the circumferential member at the turns. In another embodiment the plurality of spiral arms are engaged to the circumferential member between the turns.

In at least one embodiment, the spiral side branch section has a plurality of circumferential members and a plurality of spiral arms. Each circumferential member can be any shape, but preferably all the circumferential members of a particular spiral side branch design have the same shape. Each circumferential member has a first diameter in an unexpanded state that is different from the first diameter of the other circumferential members, i.e. a first diameter that is either larger or smaller than the first diameter of the other circumferential members. The circumferential members are arranged so that the circumferential member with the smallest first diameter, the first circumferential member, is located closest to the center of the spiral side branch opening and the circumferential member with the largest first diameter, the nth circumferential member, is located farthest away from the center of the spiral side branch section opening. The circumferential members are engaged to neighboring circumferential members by a plurality of spiral arms.

In another embodiment there are two serpentine circumferential members and a plurality of spiral arms. Each serpentine circumferential member has a first diameter in an unexpanded state. The first diameters of the two serpentine circumferential members are different, one serpentine circumferential member having a first diameter smaller than the other serpentine circumferential member. The primary branch section can be engaged to an outer support member of the spiral side branch section. The outer support member is engaged to the proximal ends of some of the plurality of spiral arms. The distal ends of some of the plurality of spiral arms are engaged to the circumferential member with the largest first diameter at the apexes of the curved undulations. The proximal ends of some of the plurality of spiral arms are engaged to the valleys of the first circumferential member. The distal ends of the second set of spiral arms are engaged to the apexes of the curved undulations of the circumferential member with the smaller first diameter. The multiple circumferential members provide circumferential support at multiple locations of the side branch lumen while the spiral arms provide flexibility and good conformability at difficult lesion areas.

In at least one embodiment, the spiral side branch section has a circumferential member, a plurality of spiral arms and a locking mechanism. The primary stent section can be engaged to an outer support member of the spiral side branch section. The outer support member is engaged to the circumferential member by a plurality of spiral segments where at least one of the spiral arms is held in place to the circumferential member by a locking mechanism. The circumferential member can be any shape. The locking mechanism allows the rings to open in only one direction. The locking center ring provides distal support for the side branch lumen.

In at least one embodiment, the spiral side branch has at least three spiral arms. The spiral arms have a width, a length and an apex. The spiral arms may be self-expanding or balloon expandable. The length of the spiral arms can vary but preferably all the spiral arms in a spiral side branch section will have the same length. In another embodiment, there may be an opening within the width of the spiral arm.

The inventive stents may be deployed to a desired bodily location by a catheter. The inventive stent may be disposed about a catheter. If a bifurcated stent is desired, the catheter used to deliver the stent can have an elongated member that extends through the opening of the side branch section of the stent. The elongated member may be a guide wire, a catheter tube or a balloon. The catheter is used to advance the stent to the desired bodily location.

In some embodiments, the invention is also directed to any of the inventive stents disclosed here in combination with or disposed about a delivery catheter. Optionally, the delivery catheter may include a first guide wire extending along the longitudinal flow path of the main body of the stent and a second guide wire extending out through the side branch support section.

The inventive stents may be made from any suitable biocompatible materials including one or more polymers, one or more metals or combinations of polymer(s) and metal(s). Examples of suitable materials include biodegradable materials that are also biocompatible. Biodegradable means that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be manufactured by methods including cutting or etching a design from a tubular stock or from a flat sheet. In the latter case, the sheet may be rolled into a stent and the edges optionally joined together via welding, gluing or any other suitable technique. The stent may also be made by fabricating individual portions of the stent and then joining the portions together. For example, the main portion of the stent and the side branch portion may be separately manufactured and then joined together via welding, the use of adhesives or any other suitable technique. The stent may also be manufactured by any other suitable technique known in the art or subsequently developed.

In some embodiments, the invention is also directed to the manufacture of the inventive stents disclosed herein. To that end, in some embodiments, the invention is directed to a method comprising the steps of providing a tube or sheet of stent material and cutting any of the inventive stent patterns disclosed herein into the tube or sheet. In the case of a sheet, the edges of the sheet may optionally be joined together. The resulting tube with the stent pattern may then be subject to standard polishing and cleaning steps as know in the art.

In some embodiments, the invention is also directed to treatment methods using any of the inventive stents disclosed herein. To that end, any of the inventive stents disclosed herein may be disposed about a stent delivery catheter. The catheter may be inserted in a bodily lumen and delivered to a desired bodily location, typically a region with a bifurcation. In the case of a balloon catheter, the stent may be expanded with a single balloon or with a plurality of balloons. In the former case, a blister balloon may be used to expand both the main branch of the stent as well as the side branch. In the latter case, a second balloon could be used to at least partially expand the side branch section of the stent into a bifurcation in a vessel and, optionally, yet another balloon could be used to fully expand the side branch. In some embodiments, a special guide wire may be used to initiate the side branch section into the bifurcation and a balloon then used to expand the side branch section. In the case of a self-expanding stent, a sheath or other restrain may be removed allowing the stent to self expand. In the case of hybrid stents, a balloon may be used to expand a portion of the stent and a sheath or other restrain withdraw from a portion of the stent. Subsequent to deployment of the stent, the catheter may be withdrawn from the body.

In some embodiments the stent, the delivery system or other portion of the assembly may include one or more areas, bands, coatings, members, etc. that may be detected by imaging modalities such as X-Ray, MRI, ultrasound, etc. In some embodiments, at least a portion of the stent and/or adjacent assembly is at least partially radiopaque. A radiopaque marker on the outer support member may facilitate placement of the stent. Optionally, a marker could be located at the spiral side branch section of the stent at a bifurcation. Similarly, a radiopaque marker on the distal end of at least one spiral arm may facilitate placement of the spiral side branch section of the stent at a bifurcation.

In some embodiments, the stent or portions thereof may include one or more mechanisms for the delivery of a therapeutic agent. In one embodiment, the side branch section may be provided with the therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising:
a plurality of interconnected framework members defining a plurality of cells, a portion of the interconnected framework members comprising a side branch structure defining an inner side branch cell, the inner side branch cell being shaped differently from other cells of the stent;
the side branch structure comprising a first serpentine ring extending around the inner side branch cell, the first serpentine ring comprising alternating struts and turns, the turns comprising alternating first inner turns and first outer turns, each strut having curvature along its length, the curvature of each strut being concave with respect to a center point of the inner side branch cell, the side branch structure further comprising a second serpentine ring extending around the first serpentine ring, the second serpentine ring comprising alternating struts and turns, the struts being concave with respect to the center point and the turns comprising alternating second inner turns and second outer turns, each first outer turn connected to a said second inner turn by a connection, each said connection having a connection width and having a connection length as measured between the turns that are connected by said connection, said connection length being less than or equal to said connection width.

2. The stent of claim 1, the struts of the first serpentine ring comprising alternating first struts and second struts, the first struts being longer than the second struts.

3. The stent of claim 1, the side branch structure further comprising a third serpentine ring extending around the second serpentine ring.

4. The stent of claim 1, the second serpentine ring comprising alternating longer struts and shorter struts.

5. The stent of claim 1, the interconnected framework members defining a plurality of serpentine bands, each serpentine band defining a wavelength;
the stent comprising end regions and a central region, the side branch structure located in the central region;
wherein serpentine bands in the central region have a shorter wavelength than serpentine bands in the end regions.

6. The stent of claim 1, wherein the turns of the first serpentine ring comprise a higher degree of curvature than the struts of the first serpentine ring.

7. The stent of claim 4, the longer struts being at least twice as long as the shorter struts.

8. The stent of claim 1, wherein a reference line extending from said center point in a side branch radial direction intersects three struts of the second serpentine ring.

* * * * *